United States Patent [19]

Kaplan et al.

[11] Patent Number: 5,713,860
[45] Date of Patent: Feb. 3, 1998

[54] INTRAVASCULAR CATHETER WITH INFUSION ARRAY

[75] Inventors: Aaron V. Kaplan, Los Altos; James R. Kermode, Sunnyvale; Enrique J. Klein, Los Altos, all of Calif.

[73] Assignee: Localmed, Inc., Palo Alto, Calif.

[21] Appl. No.: 464,153

[22] Filed: Jun. 5, 1995

Related U.S. Application Data

[60] Division of Ser. No. 241,428, May 11, 1994, Pat. No. 5,609,574, which is a continuation-in-part of Ser. No. 47,737, Apr. 15, 1993, Pat. No. 5,336,178, which is a continuation-in-part of Ser. No. 969,595, Nov. 2, 1992, abandoned.

[51] Int. Cl.$^6$ .............................................. A61M 29/00
[52] U.S. Cl. .......................... 604/96; 604/265; 604/280
[58] Field of Search ...................... 604/96, 101, 104–106, 604/265–266, 280; 606/192, 194, 198

[56] References Cited

U.S. PATENT DOCUMENTS

| | | | |
|---|---|---|---|
| 3,173,418 | 3/1965 | Baran | 128/351 |
| 3,394,705 | 7/1968 | Abramson | 128/349 |
| 3,938,502 | 2/1976 | Bom | 128/2 V |
| 4,292,974 | 10/1981 | Fogarty et al. | 128/344 |
| 4,323,071 | 4/1982 | Simpson et al. | 128/343 |
| 4,327,721 | 5/1982 | Goldin et al. | 128/207.15 |
| 4,406,656 | 9/1983 | Hattler et al. | 604/280 |
| 4,417,576 | 11/1983 | Baran | 128/207.15 |
| 4,437,856 | 3/1984 | Valli | 604/29 |
| 4,576,177 | 3/1986 | Webster | 128/660 |
| 4,661,094 | 4/1987 | Simpson | 604/53 |
| 4,681,564 | 7/1987 | Landreneau | 604/97 |
| 4,693,243 | 9/1987 | Buras | 128/207.15 |
| 4,744,790 | 5/1988 | Jankowski et al. | 604/232 |
| 4,762,129 | 8/1988 | Bonzel | 128/344 |

(List continued on next page.)

FOREIGN PATENT DOCUMENTS

| | | | |
|---|---|---|---|
| WO 87/07510 | 12/1987 | WIPO | A61M 29/02 |
| WO 88/09682 | 12/1988 | WIPO | A61M 29/02 |
| WO 92/11890 | 7/1992 | WIPO | A61M 25/00 |

(List continued on next page.)

OTHER PUBLICATIONS

Bom, N. et al. "Early and recent intraluminal ultrasound devices," 1989, Internal Journal of Cardiac Imaging 4:79–88.

Advanced Cardiovascular Systems, Inc., Temecula, California, "ACS Rx Perfusion™ Coronary Dilatation Catheter," 1990, (Product Brochure) pp. 1–23.

(List continued on next page.)

*Primary Examiner*—Corrine M. McDermott
*Attorney, Agent, or Firm*—Townsend and Townsend and Crew LLP

[57] ABSTRACT

An intravascular catheter provides means for infusing an agent into a treatment site in a body lumen and means for deploying the infusing means adjacent the treatment site which operate independently of one another. In a first embodiment, a flexible catheter body has an expansion member attached to its distal end in communication with an inflation passage, and an infusion array disposed about the expansion member in communication with one or more delivery passages. In a second embodiment, the infusion array is a separate component and slidably received over the expansion member, which may be a balloon dilatation catheter. In both embodiments, the infusion array includes a plurality of delivery conduits having laterally oriented orifices. The delivery conduits may be extended radially from the catheter body to contact a treatment site by expanding the expansion member with an inflation fluid. An agent may be introduced into the delivery passages and infused into the treatment site through orifices in the delivery conduits. The expansion member may be expanded for dilatation of the lumen before, during, or after infusion.

47 Claims, 16 Drawing Sheets

5,713,860
Page 2

U.S. PATENT DOCUMENTS

| | | | |
|---|---|---|---|
| 4,775,371 | 10/1988 | Mueller, Jr. | 604/280 |
| 4,776,337 | 10/1988 | Palmaz | 128/343 |
| 4,790,315 | 12/1988 | Mueller, Jr. et al. | 128/344 |
| 4,841,977 | 6/1989 | Griffith et al. | 128/660.03 |
| 4,850,358 | 7/1989 | Millar | 128/637 |
| 4,850,969 | 7/1989 | Jackson | 604/96 |
| 4,877,031 | 10/1989 | Conway et al. | 128/344 |
| 4,892,519 | 1/1990 | Songer et al. | 604/96 |
| 4,911,163 | 3/1990 | Fina | 606/127 |
| 4,917,097 | 4/1990 | Proudian et al. | 128/662.06 |
| 4,950,232 | 8/1990 | Ruzicka et al. | 604/43 |
| 4,976,689 | 12/1990 | Buchbinder et al. | 604/95 |
| 4,994,033 | 2/1991 | Shockey et al. | 604/101 |
| 5,000,734 | 3/1991 | Boussignac et al. | 604/96 |
| 5,007,897 | 4/1991 | Kalb et al. | 604/43 |
| 5,009,636 | 4/1991 | Wortley et al. | 604/43 |
| 5,015,232 | 5/1991 | Maglinte | 604/96 |
| 5,019,042 | 5/1991 | Sahota | 604/101 |
| 5,021,044 | 6/1991 | Sharkawy | 604/53 |
| 5,034,001 | 7/1991 | Garrison et al. | 604/53 |
| 5,041,089 | 8/1991 | Mueller et al. | 604/96 |
| 5,046,497 | 9/1991 | Millar | 128/637 |
| 5,049,132 | 9/1991 | Shaffer et al. | 604/101 |
| 5,087,244 | 2/1992 | Wolinsky et al. | 604/53 |
| 5,087,247 | 2/1992 | Horn et al. | 606/192 |
| 5,092,877 | 3/1992 | Pinchuk | 623/1 |
| 5,102,390 | 4/1992 | Crittenden et al. | 604/96 |
| 5,102,415 | 4/1992 | Guenther et al. | 606/159 |
| 5,112,303 | 5/1992 | Pudenz et al. | 604/49 |
| 5,112,305 | 5/1992 | Barath et al. | 604/96 |
| 5,117,831 | 6/1992 | Jang et al. | 128/662.06 |
| 5,163,921 | 11/1992 | Feiring | 604/247 |
| 5,180,364 | 1/1993 | Ginsburg | 604/53 |
| 5,180,366 | 1/1993 | Woods | 604/96 |
| 5,180,368 | 1/1993 | Garrison | 604/104 |
| 5,192,307 | 3/1993 | Wall | 623/1 |
| 5,203,338 | 4/1993 | Jang | 128/662.06 |
| 5,213,576 | 5/1993 | Abiuso et al. | 604/96 |
| 5,219,326 | 6/1993 | Hattler | 604/26 |
| 5,219,335 | 6/1993 | Willard et al. | 604/164 |
| 5,226,888 | 7/1993 | Arney | 604/96 |
| 5,242,396 | 9/1993 | Evard | 604/96 |
| 5,254,089 | 10/1993 | Wang | 604/96 |
| 5,257,974 | 11/1993 | Cox | 604/96 |
| 5,266,073 | 11/1993 | Wall | 623/1 |
| 5,279,565 | 1/1994 | Klein et al. | 604/105 |
| 5,281,200 | 1/1994 | Corso, Jr. et al. | 604/96 |
| 5,282,785 | 2/1994 | Shapland et al. | 604/21 |
| 5,284,473 | 2/1994 | Calabria | 604/53 |
| 5,295,962 | 3/1994 | Crocker et al. | 604/101 |
| 5,300,085 | 4/1994 | Yock | 606/191 |
| 5,306,250 | 4/1994 | March et al. | 604/104 |
| 5,308,356 | 5/1994 | Blackshear, Jr. et al. | 606/194 |
| 5,318,535 | 6/1994 | Miraki | 604/102 |
| 5,344,401 | 9/1994 | Radisch et al. | 604/96 |
| 5,358,487 | 10/1994 | Miller | 604/96 |
| 5,364,356 | 11/1994 | Höfling | 604/96 |
| 5,370,617 | 12/1994 | Sahota | 604/102 |
| 5,378,237 | 1/1995 | Boussignac et al. | 604/96 |
| 5,395,333 | 3/1995 | Brill | 604/101 |
| 5,415,637 | 5/1995 | Khosravi | 604/105 |
| 5,425,709 | 6/1995 | Gambale | 604/96 |
| 5,433,706 | 7/1995 | Abiuso | 604/96 |
| 5,439,445 | 8/1995 | Kontos | 604/96 |

FOREIGN PATENT DOCUMENTS

| | | | |
|---|---|---|---|
| WO 92/11895 | 7/1992 | WIPO | A61M 31/00 |
| WO 93/21985 | 11/1993 | WIPO | A61M 29/00 |
| WO 94/11048 | 5/1994 | WIPO | A61M 25/01 |
| WO 94/11053 | 5/1994 | WIPO | A61M 29/02 |
| WO 95/03081 | 2/1995 | WIPO | A61M 25/00 |
| WO 95/03082 | 2/1995 | WIPO | A61M 25/00 |

OTHER PUBLICATIONS

Hong, M. K. et al. "A New PTCA Balloon Catheter With Intramural Channels For Local Delivery of Drugs at Low Pressure," 1992, Supplement to Circulation, Abstracts From the 65th Scientific Sessions, vol. 86, No. 4, #1514.

EndoSonics, Pleasanton, California, "The Cathscanner® Intracoronary Imaging System," 1992, (Product Brochure).

SCIMED®, Maple Grove, Minnesota, "Dispatch™," 1994, (Product Brochure).

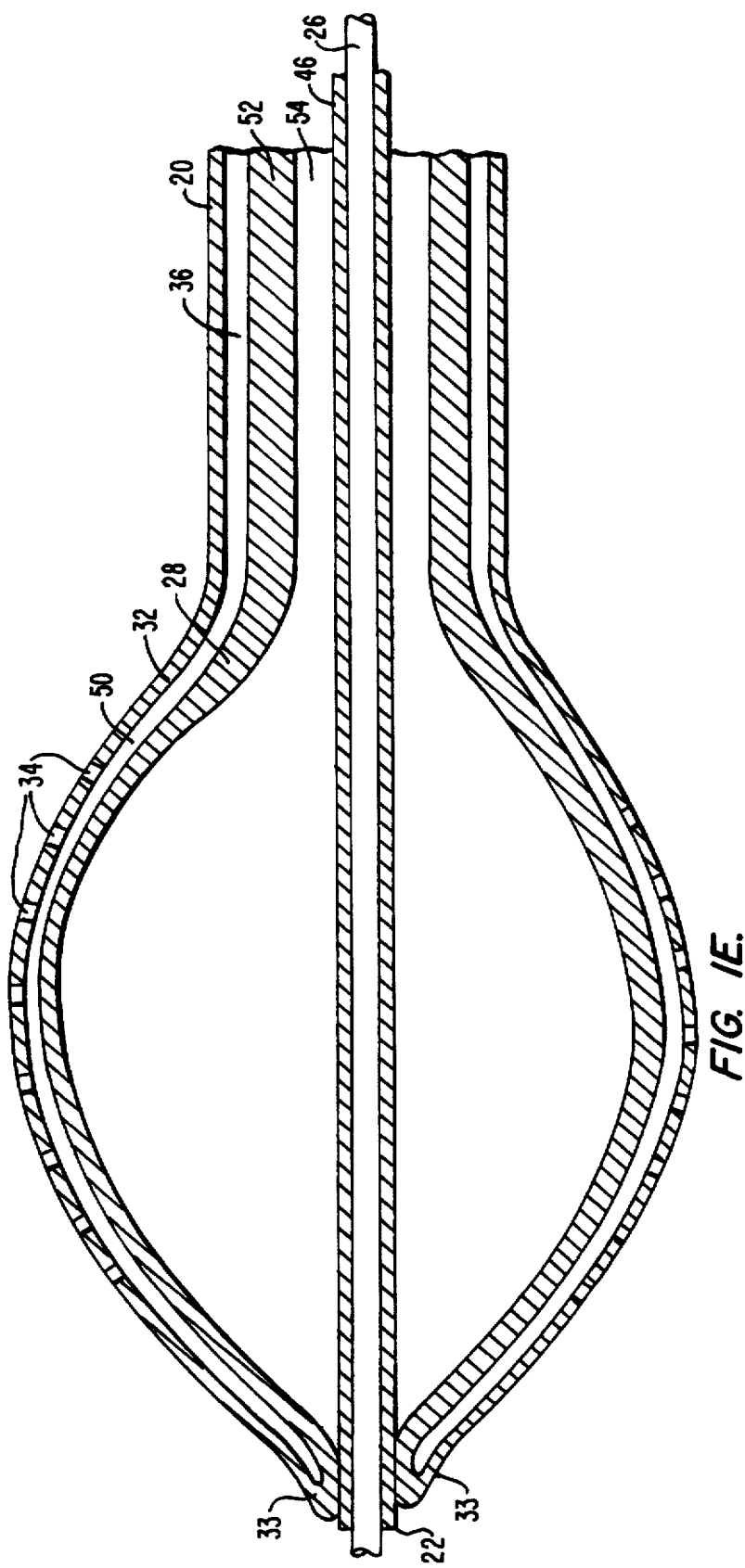
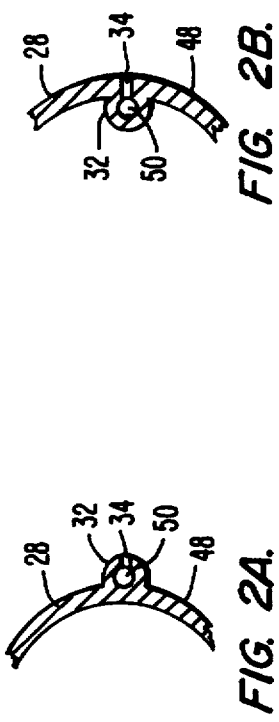

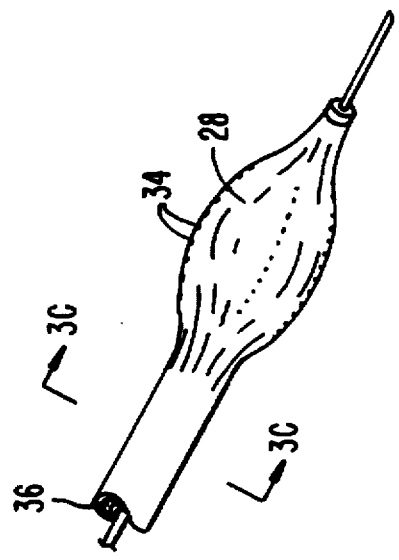
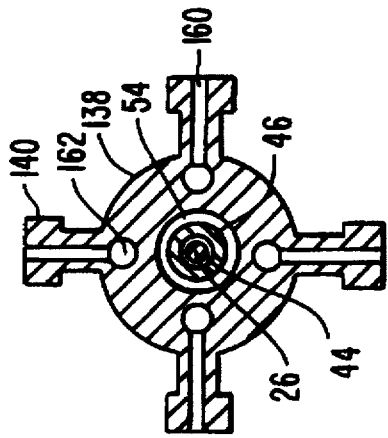
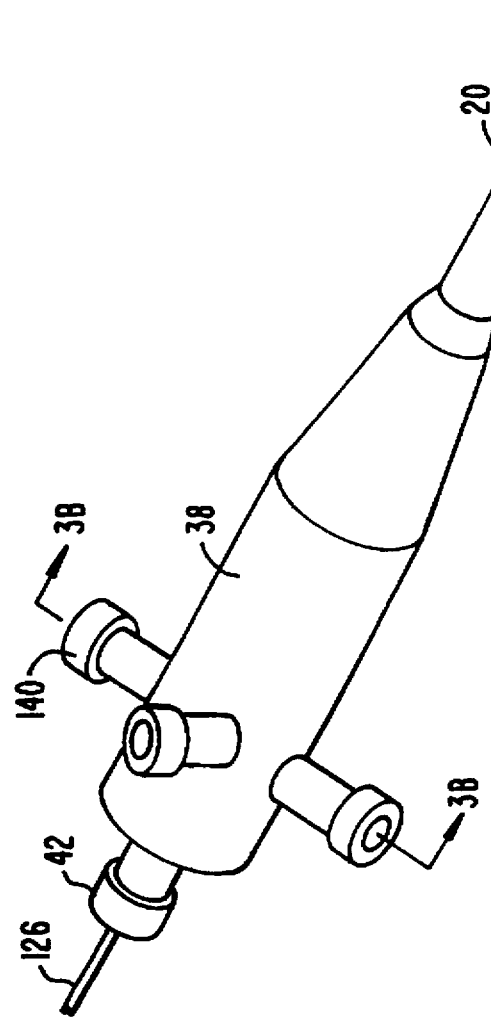
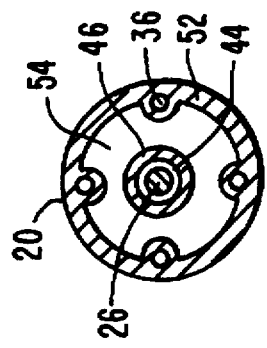

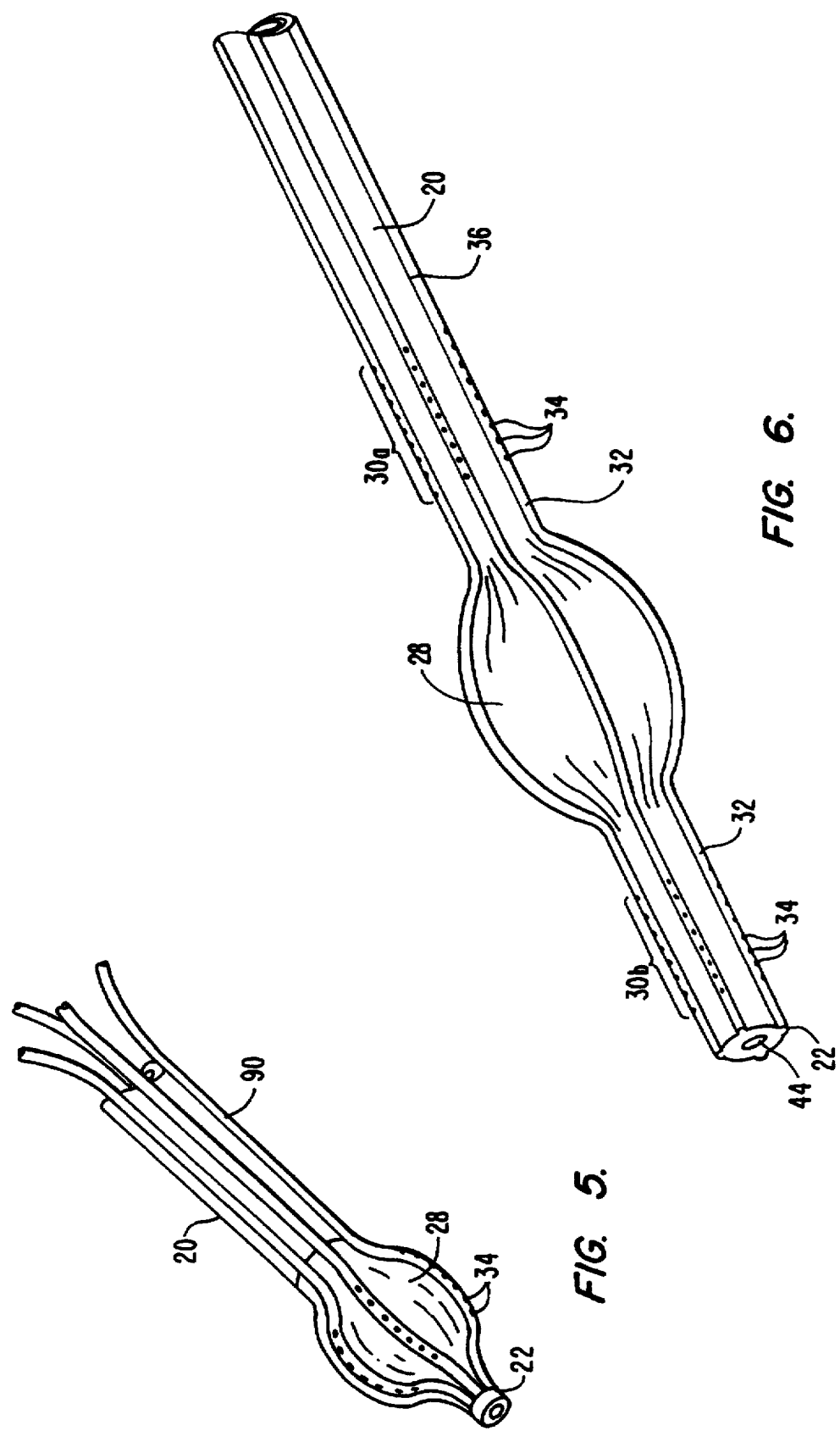

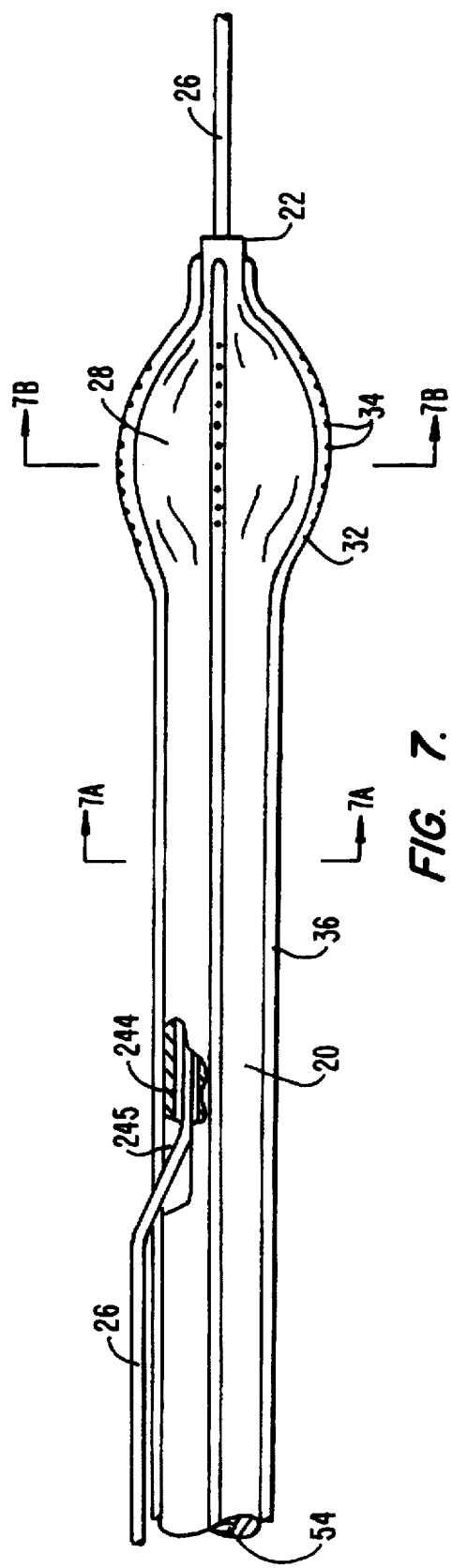
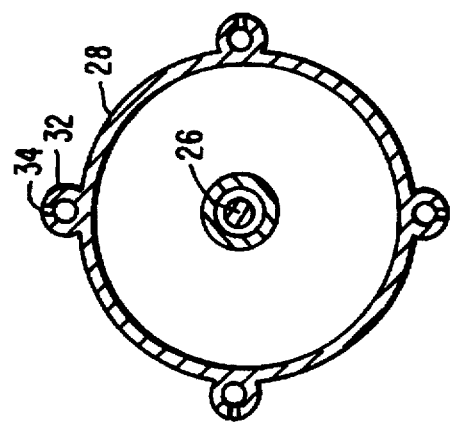
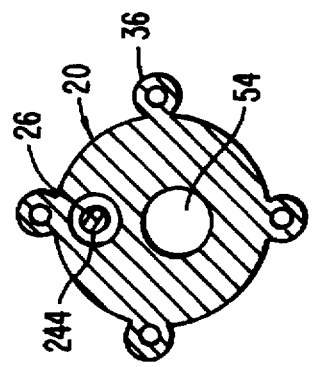
FIG. 7.
FIG. 7A.
FIG. 7B.

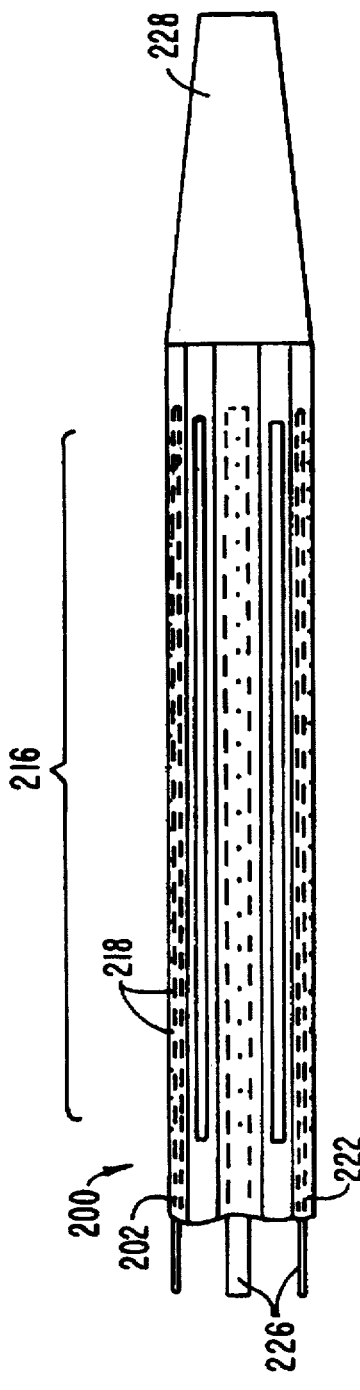
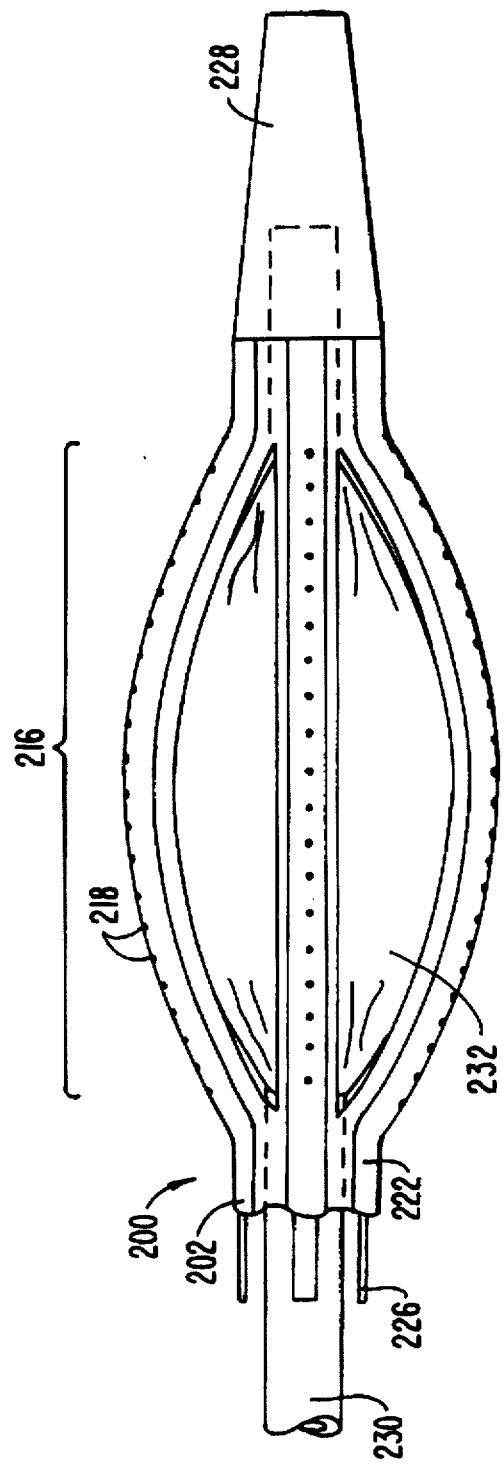
FIG. 10A.
FIG. 10B.

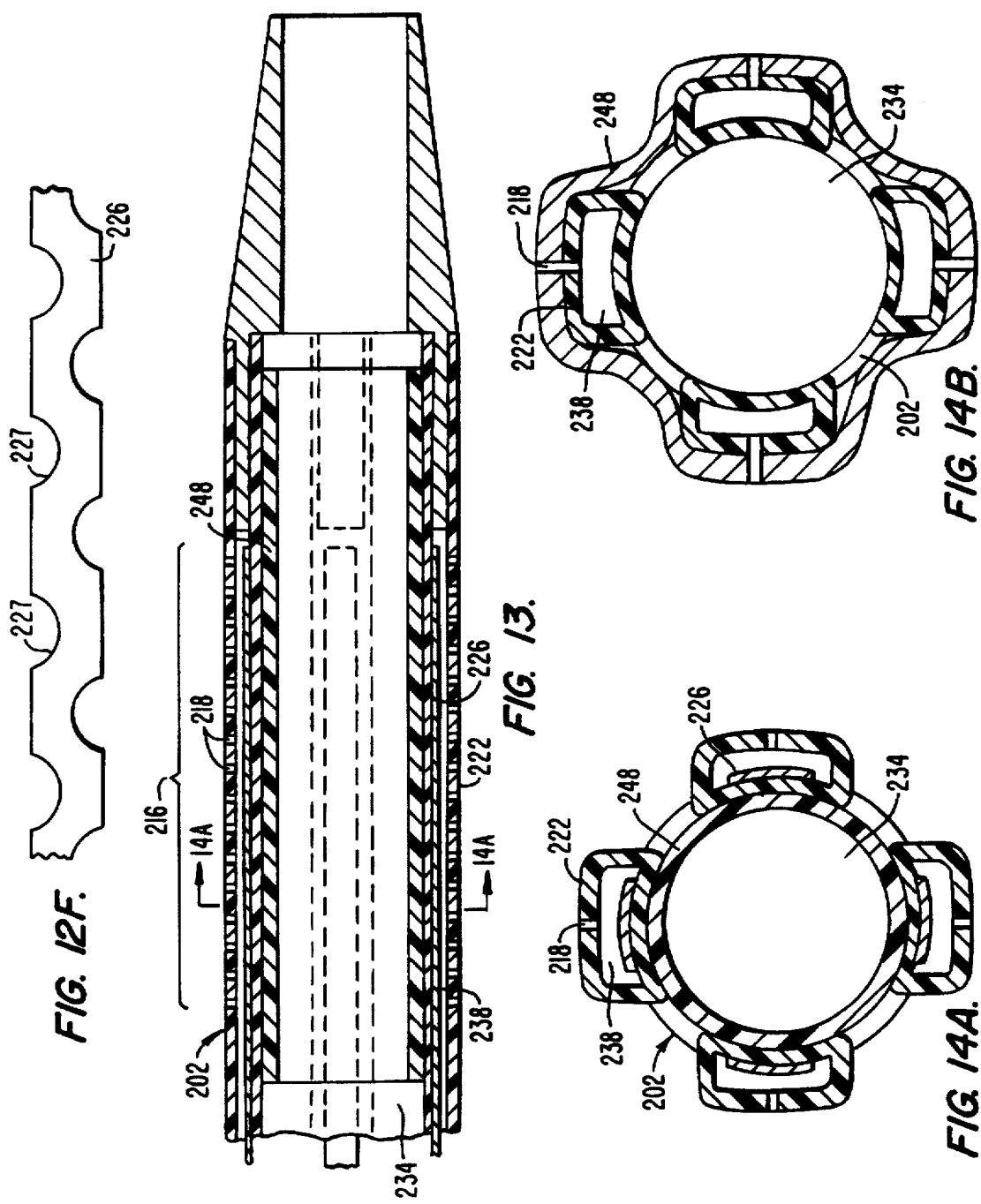

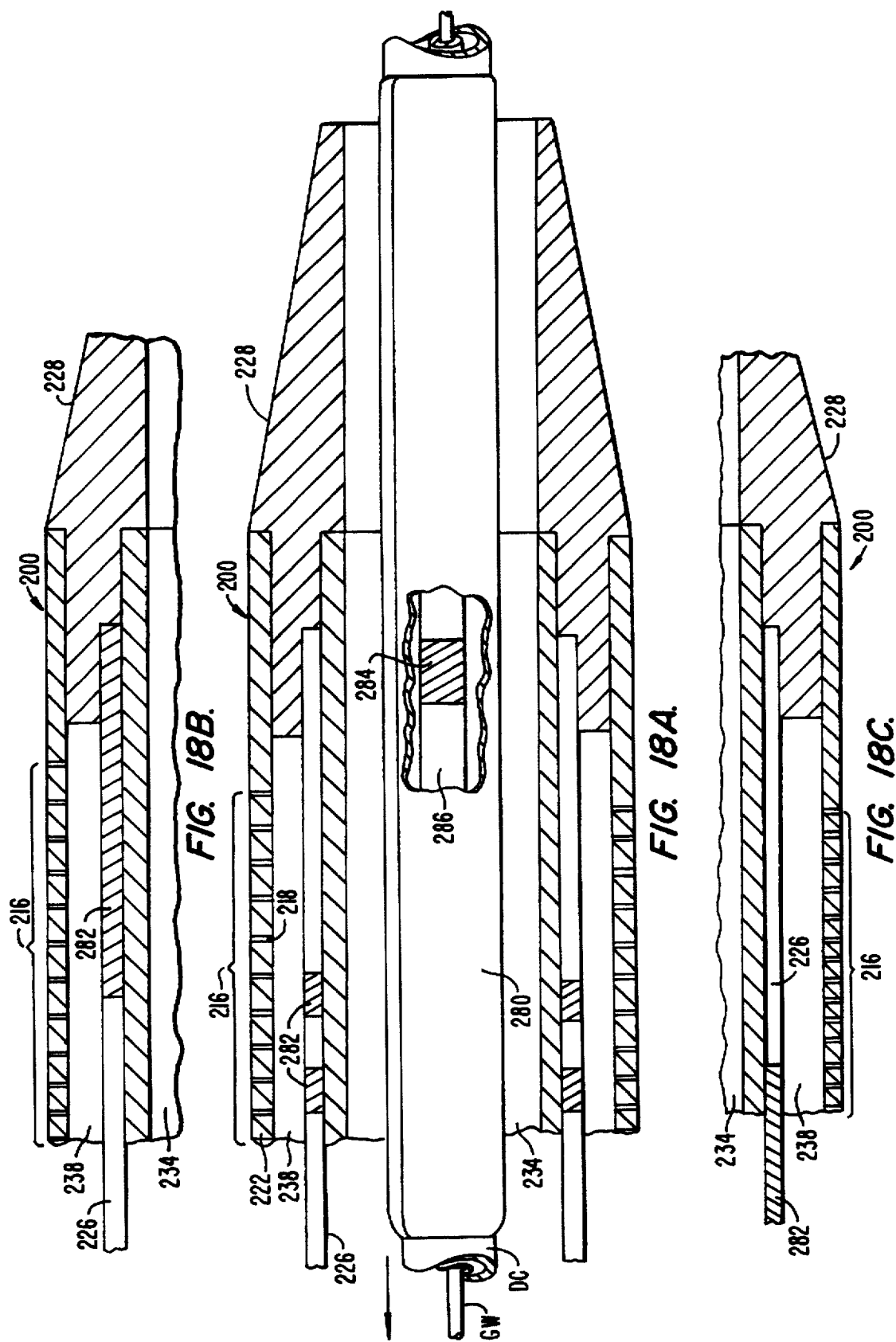

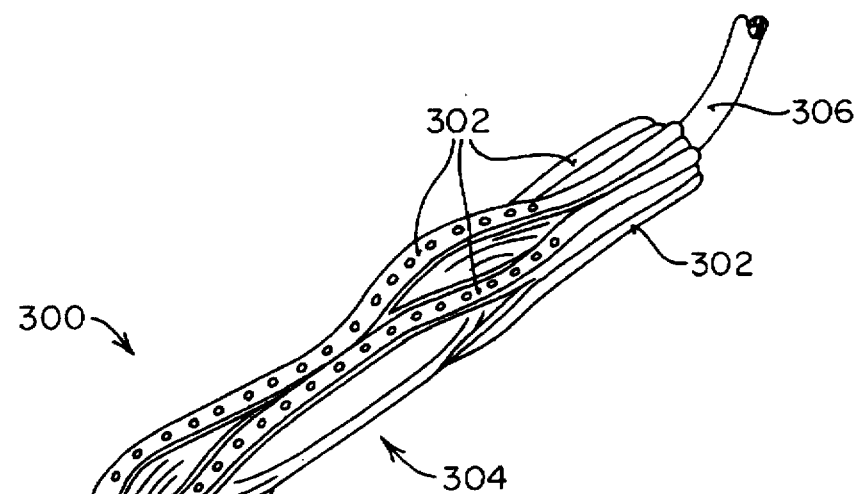
FIG_19
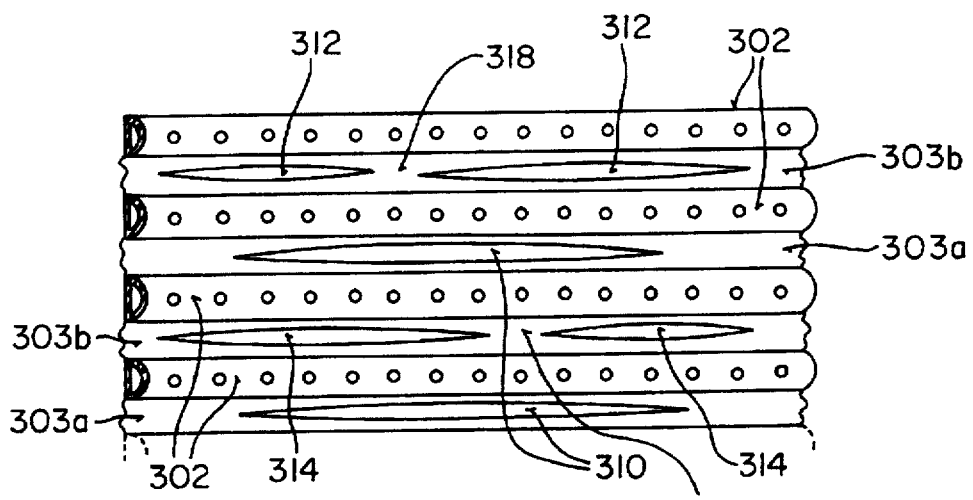
FIG_20

INTRAVASCULAR CATHETER WITH INFUSION ARRAY

CROSS-REFERENCE TO RELATED APPLICATIONS

This is a divisional of application Ser. No. 08/241,428, filed May 11, 1994, now U.S. Pat. No. 5,609,574, which was a continuation-in-part of application Ser. No. 08/047,737, filed Apr. 15, 1993, now U.S. Pat. No. 5,336,178, which was a continuation-in-part of application Ser. No. 07/969,595, filed Nov. 2, 1992, now abandoned, the complete disclosures of which are incorporated herein by reference.

BACKGROUND OF THE INVENTION

This invention relates generally to drug-delivery devices, and more specifically to intravascular catheters for delivery of therapeutic agents from within a lumen of a blood vessel or other body organ.

In percutaneous transluminal angioplasty procedures, a catheter having an expandable distal end, usually in the form of a balloon, is positioned in a lumen of a blood vessel with the distal end disposed within a stenotic atherosclerotic region of the vessel. The expandable end is then expanded to dilatate the vessel and restore adequate blood flow through the region of stenosis.

Whereas angioplasty has gained wide acceptance, it continues to be plagued by two major problems, abrupt closure and restenosis. Abrupt closure refers to the acute occlusion of a vessel immediately after or within the initial hours following the dilatation procedure. This type of complication, occurring in approximately one in twenty cases, frequently results in myocardial infarction and death if blood flow is not quickly restored. The primary mechanisms of abrupt closures are arterial dissection and/or thrombosis. It is postulated that the ability to deliver agent (e.g. an antithrombotic drug) directly into the arterial wall at the time of angioplasty would reduce the incidence of thrombotic acute closure.

Restenosis refers to the re-narrowing of an artery after an initially successful angioplasty. Restenosis usually occurs within the initial six months after angioplasty. It is postulated that the delivery of certain agents directly into the arterial wall would interrupt the cellular events leading to restenosis.

The potential utility of local intramural drug delivery is not limited to atherosclerotic coronary artery disease. Other sites of atherosclerosis (e.g. renal, iliac, femoral, distal leg and carotid arteries as well as saphenous vein grafts, synthetic grafts and arteriovenous shunts used for hemodialysis) would also be appropriate for local intramural drug delivery. Local intramural therapy may also prove efficacious in non-arterial structures, including the prostate via the prostatic urethra (benign prostatic hypertrophy, prostatitis and adenocarcinoma), fallopian tubes via its lumen (strictures), and brain parenchyma (Parkinson's Disease).

At present, intravenous medications are delivered systemically by vein or regionally (e.g. intracoronary infusion). Systemic delivery is generally not well suited to the treatment of disease entities with a single site or several discrete sites of interest (e.g., coronary artery disease) in that it necessitates: (1) exposing sites other than the site of interest to medication where it may have an adverse effect; (2) infusing sufficient quantities of agent to achieve the concentration throughout the entire volume of distribution; and (3) exposing the agent to degradation and elimination by one or more organ systems remote from the site of interest. Furthermore, the tissue concentration that can be achieved at the site of interest is often limited by the effects of the agent at distant sites. Local intramural delivery obviates these problems. Therefore, it is of particular importance to deliver the therapeutic agent directly to the treatment site by contact with or penetration into the tissue, rather than simply releasing the agent into the blood stream in the vicinity of the treatment site.

While various catheters have been developed for delivery of agents to a treatment site within a vessel or organ lumen, such devices have suffered from certain drawbacks. In particular, known agent delivery catheters generally do not permit delivery of an agent directly to a treatment site independently of the deployment of the delivery mechanism adjacent the lumen wall. For example, known agent delivery catheters frequently employ an expandable member such as a balloon which is expanded near the treatment site and brought into contact with the lumen wall. A therapeutic agent is usually delivered through pores on the surface of the balloon. In such devices, the pressurized fluid which expands the balloon is also the vehicle for the agent. Therefore, the balloon cannot be expanded without expelling the drug/vehicle mixture. This scheme is inefficient, in that agent is expelled before the periphery of the balloon is adjacent to the lumen wall. This scheme also prevents delivery of agent without at least partly expanding the balloon. The deployment mechanism (i.e. balloon expansion) and the drug delivery mechanism are inextricable linked.

Thus, where it would be desirable to dilatate a region of stenosis in an artery without simultaneously infusing an agent, known drug delivery catheters are of little use. Moreover, where it would be desirable to infuse an agent within a body lumen without deploying the balloon, known drug delivery catheters are similarly ineffective. Furthermore, in devices which employ the agent/vehicle mixture to pressurize and expand the balloon, the reversal of fluid flow required to retract the balloon tends to draw blood into the device, preventing further use of the device until the blood has been expelled. Typically, this prevents multiple treatments without withdrawing the catheter for purging or replacement.

A further drawback of known drug delivery devices stems from their incapacity for selective delivery of agent to various sectors of an organ lumen. Such directional treatment may be advantageous, where, for example, only a particular portion of a vessel wall is diseased and infusion to non-diseased regions is undesirable. Further, in certain procedures, the ability to selectively infuse different agents in different areas of the lumen may be advantageous. In known devices, it is not possible to deliver agent selectively into a particular sector of the artery, or to deliver two or more different agents into different sectors simultaneously.

Moreover, known drug delivery catheters which infuse an agent through a porous balloon generally release the agent at relatively low pressures so as to merely bathe or coat the vessel wall where it is contacted by the infusion member. With such devices, the agent will generally not penetrate the lumen wall and may not provide effective therapy. Treatment would be more effective if the therapeutic agent were delivered at pressures sufficient to achieve penetration to the adventitial layer of the organ wall.

A drug delivery catheter is therefore desired which can be used to administer therapeutic agents to a treatment site within a lumen of a body organ by direct contact with the lumen wail tissue. Most desirably, the drug delivery catheter will be deployable against the treatment site independently of the delivery of the agent to the site. The catheter should also allow dilatation of a vessel with or without delivery of a drug or other therapeutic agent. Preferably, the catheter should be capable of injecting an agent at pressures sufficient to penetrate the adventitial layer of an artery. In addition, the catheter should allow selective infusion of an agent in various radial directions, and simultaneous infusion of two or more different agents in different radial directions. The catheter should further be useful for treatment of blood vessels as well as a variety of other body organs.

DESCRIPTION OF THE BACKGROUND ART

Balloon-tipped catheters appropriate for angioplasty treatment procedures are described in, for example, U.S. Pat. No. 5,041,089, U.S. Pat. No. 4,323,071, U.S. Pat. No. 4,292,974, U.S. Pat. No. 4,762,129, and U.S. Pat. No. 4,775,371. A catheter for locally applying medication to the wall of a blood vessel or other lumen is described in U.S. Pat. No. 5,087,244, the catheter having a balloon near its distal end which is expanded with a medication, which then flows through minute holes in the balloon surface at a low flow rate. U.S. Pat. No. 4,994,033 describes an intravascular drug delivery catheter having a pair of expansion members concentrically arranged near its distal end wherein an agent is delivered to the outer expansion member, after which the inner expansion member is expanded, thereby expanding the outer member against the vessel wall and forcing the agent through minute holes in the outer member to bathe the vessel wall. U.S. Pat. No. 5,021,044 describes an intravascular drug delivery catheter having a plurality of holes on the outer surface of the catheter body through which an agent may be delivered to a site within a vessel. U.S. Pat. No. 5,112,305 describes a catheter for delivery of therapeutic agents to an interior wall of a vessel, the catheter having a balloon near its distal end with tubular extensions capable of projecting from its outer surface. An agent is delivered to the balloon which both expands the balloon and flows through the tubular extensions into the vessel wall. Other drug delivery devices are described in U.S. Pat. No. 4,693,243, U.S. Pat. No. 4,406,656, U.S. Pat. No. 5,015,232, U.S. Pat. No. 5,087,247, and U.S. Pat. No. 4,850,969.

SUMMARY OF THE INVENTION

The present invention provides an intravascular catheter for administering a therapeutic agent to a treatment site in the wall of a vessel. The catheter will have particular usefulness in treating arterial stenoses in conjunction with angioplasty, but will have further application in treating diseases affecting other body organs, such as the prostate, biliary ducts and genital-uretal-system. The catheter of the present invention is particularly advantageous over known devices because it permits deployment of the delivery mechanism adjacent to the treatment site independently of the delivery of the agent to the treatment site. The invention thereby facilitates dilatation to be performed with or without infusion of an agent, as well as infusion of an agent before, during, after, or without dilatation. The catheter of the present invention further permits directional infusion of one or more agents within a body lumen. Moreover, the catheter improves the effectiveness of drug treatment by infusing the agent at pressures sufficient to achieve penetration into the adventitial layer of the organ.

In a specific embodiment, an apparatus for infusing an agent to a treatment site in a body lumen comprises a catheter body having a distal end, a proximal end and first and second passages therebetween; a guidewire extending from the distal end of the catheter body; an expansion member attached to the catheter body near the distal end, the interior of the expansion member being in fluid communication with the first passage; and an infusion array in communication with the second passage and disposed adjacent a lateral surface of the expansion member so as to be deployable adjacent to the treatment site by deployment of the expansion member, wherein the infusion array is operable for infusing an agent to the treatment site independently of deployment of the expansion member.

In a preferred embodiment, the infusion array comprises at least a first tubular delivery conduit having a plurality of orifices on a surface thereof and an axial passage which is in communication with the second passage in the catheter body. Usually, the infusion array will include a plurality of tubular delivery conduits disposed at various positions about the periphery of the balloon. The orifices in the delivery conduits will typically be radially-oriented so as to open directly onto the treatment site when the conduits are positioned adjacent to the vessel wall.

The delivery conduits may be connected to a single delivery passage in the catheter, but in a preferred embodiment, the catheter body will include a plurality of delivery passages, each passage being in communication with one delivery conduit. An agent may be infused through selected delivery conduits by delivering the agent through the corresponding delivery passage or passages. In this way, infusion may be performed at selected directions, and two or more agents may be infused through selected delivery conduits simultaneously.

The expansion member may comprise a balloon similar to those of conventional balloon dilatation catheters. In a preferred embodiment, the expansion member and delivery conduits will be integrated into a single, monolithic extrusion, the conduits comprising passages in or along the wall of the expansion member. Alternatively, the delivery conduits may be structurally separate from the balloon and disposed on its exterior surface.

The expansion member may alternatively comprise a balloon fixed to an entirely separate dilatation catheter removably disposed in an axial passage through the catheter body. In this embodiment, the delivery conduits will usually be mounted to an expandable support member disposed about an opening in the catheter body in which the balloon of the removable dilatation catheter resides.

The expansion member will be expanded using an expansion fluid supplied through the first passage in the catheter body. Because the expansion member is fluidly isolated from the delivery conduits, the expansion fluid will not include the infusion agent, which is infused separately via the device.

Deployment of the expansion member brings its lateral wall along with the delivery conduits of the infusion array adjacent to the treatment site. The expansion member is used only for deploying the infusion array adjacent the vessel wall and/or dilatating the vessel, and plays no part in infusing an agent through the infusion array. The infusion conduits retain their fluid-conducting capacity whether positioned against the treatment site or retracted toward the center catheter body. Thus, an agent may be infused through the infusion array irrespective of whether the expansion member is expanded or retracted.

The infusion array will be configured to infuse an agent at sufficient pressure to penetrate to a depth of at least the media, and preferably into the adventitia of the arterial wall. In a preferred embodiment, the delivery conduits of the infusion array will be composed of polyester, with an inner diameter on the order of 0.1–0.2 mm, a wall thickness on the order of 0.05–0.1 mm, and orifices of 10–50 μm in diameter. The use of a plurality of delivery conduits of relatively high stiffness and small cross-section, each supplied through independent delivery passages from the proximal end of the device, rather than a single delivery passage with a manifold at the distal end, provides a stiffer hydraulic system. This allows for the infusion of more precisely-metered doses than is possible in known devices and results in a substantially more efficient method of agent delivery.

In a preferred aspect of the apparatus of the present invention, the delivery conduits will be formed in or on a sleeve which defines an expandable support member. The sleeve may be elastic or inelastic, usually being inelastic and formed with radial expansion slits, as described below. The delivery conduits will usually, but not necessarily, be axially aligned on the sleeve and be circumferentially spaced-apart by web portions of the sleeve. The web portions will be at least partially split to facilitate radial expansion by the internal expansion member, typically a separate balloon catheter. The sleeve may also be a tubular elastomeric sleeve where the sleeve is axially split between at least some adjacent pairs of the delivery conduits. Preferably, the tubular elastomeric sleeve will be fully split between the adjacent pairs and partially split between others. Alternatively, the tubular elastomeric sleeve may be fully split to form two separate sections between adjacent pairs of the delivery conduits. The elastomeric sleeve may have four attached delivery conduits with the elastomeric tubular sleeve being split fully between first opposed conduit pairs and into two sections between second opposed conduit pairs. In some cases, the splits between the second opposed conduit pairs may remain connected near their middles. In a particularly preferred embodiment, the pattern of splits will be selected to provide a relatively uniform circumferential distribution of the delivery conduits along the expanded length of the sleeve. For example, at least some of the splits may be discontinuous. In an exemplary embodiment, an infusion array includes four delivery conduits circumferentially spaced-apart by four web portions. Two opposed web portions will be split along most or all of their lengths while the remaining two opposed web portions will remain attached at or near their middle sections. Such a pattern insures that the circumferential distribution of the delivery conduits will be consistent and repeatable upon the deployment of the internal expansion member, which in turn will often provide more uniform drug delivery fluxes along the length of the array.

In a preferred aspect of the method of the present invention, an agent delivery catheter is positioned in a blood vessel with an infusion array at the distal end of the catheter near the treatment site. An expansion member at the distal end of the catheter, which is fluidly isolated from the infusion array, is deployed so as to position the infusion array adjacent a treatment site in the vessel lumen. Thereafter, an agent is delivered to the infusion array through at least one delivery passage in the catheter. The agent is then infused into the treatment site through a plurality of orifices in the infusion array.

In a particular embodiment, the agent is delivered from the proximal end of the catheter through a plurality of separate delivery passages to a plurality of delivery conduits at the distal end of the device, the orifices of the infusion array being arranged on the outermost surfaces of the delivery conduits. In this way, delivery of the agent to each delivery conduit may be controlled independently. Thus, an agent may be infused through a first delivery conduit without infusing the agent through a second delivery conduit, or a first agent may be infused through a first delivery conduit while a second agent is infused through a second delivery conduit.

In a specific embodiment, the method will be used for treatment of coronary artery disease, wherein the catheter is positioned with the infusion array near a stenotic or otherwise diseased site in an artery. Usually, a fixed guidewire mounted at the distal end of the catheter, or a movable guidewire extending through a guidewire passage in the catheter, will be used to guide the catheter into the vessel. The expansion member may be deployed to dilatate the artery for restoration of adequate blood flow, with or without infusion of an agent through the infusion array. Before, during, after, or without dilatation, one or more agents may be infused through the infusion array into the treatment site.

In alternative embodiments, the method of the invention may be used for treatment of various other body organs, including the biliary ducts, or the genital-uretal organs.

A further understanding of the nature and advantages of the invention may be realized by reference to the remaining portions of the specification and the drawings.

BRIEF DESCRIPTION OF THE DRAWINGS

FIG. 1E is a longitudinal cross-section of the distal end of the catheter of FIG. 1 cutting through two drug delivery conduits.

FIGS. 2A–2C are transverse cross-sections of a portion of the expansion member and delivery conduits of the catheter of FIG. 1., showing various alternative embodiments thereof.

FIG. 3A is a perspective view of a further embodiment of an agent delivery catheter constructed in accordance with the principles of the present invention.

FIG. 3B is a transverse cross-section of a proximal end of the catheter of FIG. 3A.

FIG. 3C is a transverse cross-section of the catheter shaft of the catheter of FIG. 3A.

FIG. 5 is a perspective view of a further embodiment of an agent delivery catheter constructed in accordance with the principles of the present invention.

FIG. 6 is a perspective view of still another embodiment of a drug delivery catheter constructed in accordance with the principles of the present invention.

FIG. 7 is a side view of a distal end of a further embodiment of a catheter constructed in accordance with the principles of the present invention.

FIGS. 7A–7B are transverse cross-sections of the catheter of FIG. 7 through the catheter shaft and through the expansion member, respectively.

FIGS. 10A and 10B are side elevational views of a distal portion of the catheter of FIG. 9 in undeployed and deployed configurations, respectively.

FIG. 12F is a top elevational view of a further embodiment of the stiffening element in the catheter of FIG. 9.

FIG. 13 is a side cross-section of a further embodiment of the infusion array of the catheter of FIG. 9 wherein the delivery conduits are secured to the periphery of an elastomeric sleeve.

FIG. 14A is a transverse cross-section of the infusion array of FIG. 13.

FIG. 14B is a transverse cross-section through the infusion array wherein the elastomeric sleeve is disposed external to the delivery conduits.

FIGS. 18A–18C are side cross-sectional views of a distal portion of the infusion catheter of FIG. 9 illustrating the radiopaque markers on the stiffening elements.

FIG. 19 is a perspective view of the distal end of an alternative infusion array constructed in accordance with the principles of the present invention received over a balloon catheter.

FIG. 20 is a planar projection of the infusion array of FIG. 19, where the tubular array has been "unrolled" to show a pattern of splits between adjacent pairs of infusion conduits.

DESCRIPTION OF SPECIFIC EMBODIMENTS

Figure 1:
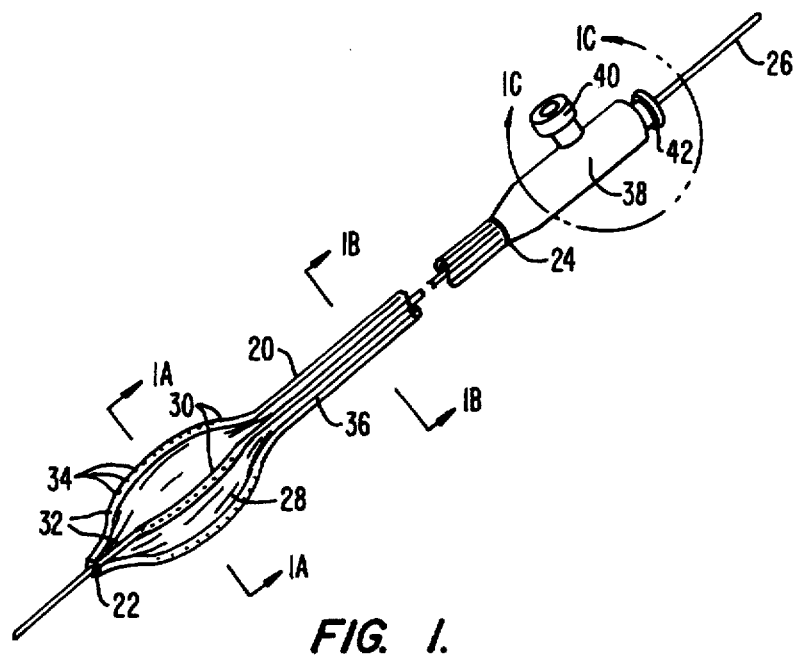
FIG. 1 is a perspective view of an agent delivery catheter constructed in accordance with the principles of the present invention.

Referring to FIG. 1, the intravascular drug delivery catheter of the present invention includes an elongate flexible shaft 20 having a distal end 22 and a proximal end 24. A movable guide wire 26 extends through the catheter and beyond its distal end 22. An expansion member 28 is attached to the catheter shaft 20 near distal end 22. An infusion array 30 comprising delivery conduits 32 and orifices 34 is disposed about the exterior surface of expansion member 28. Conduits 32 are in communication with delivery passages 36 in catheter shaft 20. A housing 38 is mounted to proximal end 24 of catheter shaft 20. Housing 38 includes an agent introduction port 40 and an inflation fluid introduction port 42.

Figure 1A:
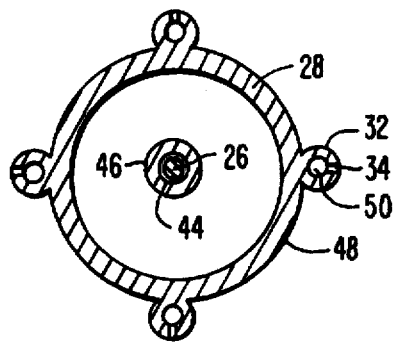
FIG. 1A is a transverse cross-section of a distal portion of the catheter of FIG. 1.

A distal portion of the catheter will now be described with reference to FIGS. 1A and 1E. A guidewire passage 44 is disposed centrally in shaft core 46, through which guidewire 26 is slidably disposed. Expansion member 28 surrounds shaft core 46, with delivery conduits 32 disposed about its periphery. Delivery conduits 32 include an axial passage 50 in communication with orifices 34. Distal ends 33 of delivery conduits 32 are sealed. In a preferred embodiment, delivery conduits 32 and expansion member 28 comprise a single integrated, monolithic extrusion, with the delivery conduits forming longitudinal passages in the wall of the expansion member.

It will be understood that the catheter of the present invention may have any of a variety of guidewire configurations. For example, as shown in FIGS. 7, 7A and 7B, rather than being disposed centrally in the shaft core, guidewire passage 244 may be offset from the center axis independent of and parallel to inflation lumen 54. Moreover, such a guidewire passage need not extend through the entire length of shaft 20, but may instead have a lateral opening 245 at a point along shaft 20 through which guidewire 26 exits the offset guidewire passage 244 and shaft 20, such that guidewire 26 and shaft 20 are independent of each other at the proximal end of the device. Such an offset guidewire is described in U.S. Pat. No. 4,748,982, the complete disclosure of which is incorporated herein by reference. Furthermore, a fixed guidewire (not shown) extending from distal end 22 may be used in lieu of movable guidewire 26.

As illustrated in FIGS. 2A–2C, delivery conduits 32 may be integrated with expansion member 28 at various positions relative to exterior surface 48. In the embodiment of FIG. 2A, delivery conduits 32 are disposed exterior to surface 48 so as to protrude therefrom. In the embodiment of FIG. 2B, delivery conduits 32 are disposed primarily in the interior of expansion member 28 with orifices 34 extending through the thickness of the expansion member, such that surface 48 has a substantially smooth contour about the periphery of the expansion member. FIG. 2C shows another embodiment wherein delivery conduits 32 are disposed centrally in the wall of expansion member 28, producing only a slight protuberance on surface 48.

The number of delivery conduits 32 may vary from one to eight or more, but in a preferred embodiment, there will be four delivery conduits spaced at approximately 90 degrees about the circumference of expansion member 28. Delivery conduits 32 may be disposed in various arrangements about the periphery of expansion member 28, both symmetrically and asymmetrically. For example, the delivery conduits may be arranged such that a majority or all of the conduits are on one side of the expansion member. Or, the delivery conduits may be arranged with two pairs of closely-spaced conduits on opposing sides of expansion member 28. Moreover, the delivery conduits may be of different diameters, and may have varying sizes, shapes and arrangements of orifices 34. Orifices 34 may be in a single row, but may also be in a non-linear arrangement, or in multiple rows or groups on each delivery conduit.

Delivery conduits 32 will preferably have sufficient rigidity in the transverse direction so as to remain uncollapsed when positioned by expansion member 28 against a wall of artery.

Delivery conduits 32 and orifices 34 will preferably be configured to infuse an agent at sufficient pressure to penetrate into the adventitial layer of the organ wall. Usually, the device will achieve penetration to at least the media. Pressures of at least 4 atmospheres are generally necessary to achieve such penetration. The present invention, in an exemplary embodiment, will infuse the agent at a pressure of up to 10 atmospheres or more. This will be accomplished by delivering the agent under pressure from the proximal end of the catheter through delivery passages 36. In addition, the geometry and material of the delivery conduits 32 will be selected to facilitate penetrative infusion. In a preferred embodiment, the delivery conduits 32 will be composed of polyester, with an interior diameter of about 0.1–0.2 mm, and a wall thickness of about 0.05–0.10 mm. Orifices 34 will have a diameter in the range of 10 to 50 μm.

Figure 1B:
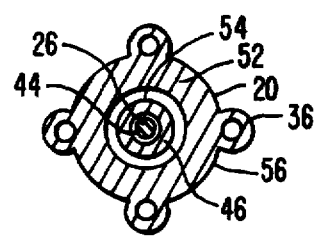
FIG. 1B is a transverse cross-section of the catheter shaft of the catheter of FIG. 1.

Referring now to FIG. 1B, catheter shaft 20 proximal to expansion member 28 includes shaft core 46 with guidewire 26 extending through guidewire passage 44. An outer body 52 of the catheter shaft surrounds an inflation passage 54. Delivery passages 36 and outer body 52, in a preferred embodiment, comprise a monolithic extrusion, with a variety of possible configurations. In the embodiment of FIG. 1B, the delivery conduits 36 are disposed on the exterior surface 56 of outer body 52. Other possible configurations will be similar to those illustrated in FIGS. 2B and 2C and described above in connection with delivery conduits 32. Further embodiments are shown in FIGS. 4A–4E and FIG. 5, described more fully below.

Expansion member 28 may be adhesively attached to catheter shaft 20, but will preferably be formed as a single extrusion, along with delivery passages 36 and delivery conduits 32, forming a continuous, monolithic structure from proximal end 24 to distal end 22. While known catheter fabrication techniques have been used to form a balloon at the distal end of a tubular shaft, it is heretofore unknown to form a balloon at the distal end of a monolithic extruded structure with delivery conduits within the wall of the balloon and delivery passages within the wall of the shaft in communication with the delivery conduits.

Figure 1C:
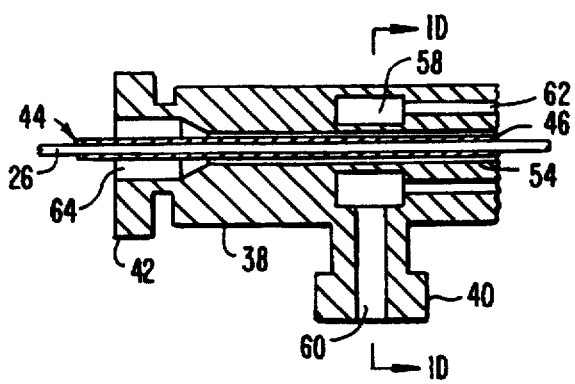
FIG. 1C is a side cross-section of the proximal end of the catheter of FIG. 1.
Figure 1D:
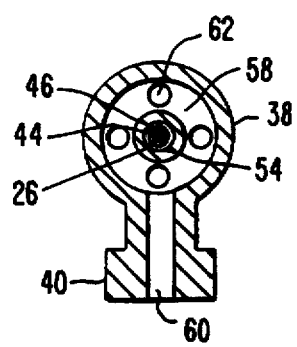
FIG. 1D is a transverse cross-section through the proximal end of the catheter of FIG. 1C.

Referring now to FIGS. 1C and 1D, housing 38 includes an annular manifold 58 in communication with a passage 60 through agent introduction port 40. Distribution passages 62 extend distally from manifold 58 to catheter body 20, where they connect to delivery passages 36. Inflation passage 54 extends through housing 38 and connects to passage 64 in inflation port 42. Shaft core 46 is disposed within inflation passage 54, with guidewire 26 extending through guidewire passage 44.

A further embodiment of the catheter of the present invention is illustrated in FIGS. 3A–3C. In this embodiment, housing 38 at the proximal end of the device has a plurality of agent introduction ports 140, each introduction port being in communication with one of delivery passages 36 in catheter shaft 20 via connection passages 162. In other respects, the catheter is much like that described above in connection with FIGS. 1A–1E, except that delivery passages 36 and delivery conduits 32 (not visible) have the configuration illustrated in FIGS. 2B and 3C, respectively.

By providing separate introduction ports 140 for each delivery passage 36 and delivery conduit 32, the invention as embodied in FIGS. 3A–3C permits directional infusion of one or more agents through orifices 34 in different delivery conduits 32 of infusion array 30. This may be advantageous where only a particular portion of a vessel is to be treated, and infusion to other portions is undesirable. Directional infusion may further be useful to infuse a first agent through one or more delivery conduits 32 at selected directions, while simultaneously infusing one or more other therapeutic agents through other delivery conduits. In this way, for example, a growth-inhibiting agent may be delivered to a stenotic region of the vessel through the delivery conduits on one side of the catheter, while an anti-coagulant is delivered through the delivery conduits on another side of the catheter.

A further embodiment of the catheter of the present invention, illustrated in FIGS. 4A–4E, comprises a separate dilatation catheter 70 of conventional construction removably disposed in an axial passage 72 in catheter body 20. An expandable support member 74 is attached to the distal end of catheter body 20, more clearly illustrated in FIGS. 4C and 4E. Support member 74 comprises a tubular structure having a plurality of separate support sections 75. Delivery conduits 32 are disposed on a lateral surface of support sections 75, and are in communication with delivery passages 36 in catheter body 20. Orifices 34 are disposed on a lateral surface of delivery conduits 32, with distal ends 33 of delivery conduits 32 sealed. While support member 74 and delivery conduits 32 are shown as separate structures mounted to catheter body 20, it will be understood that catheter body 20, support member 74 and delivery conduits 32 may comprise a single (monolithic) extrusion, as described above in connection with FIGS. 1A–1E.

Figure 4A:
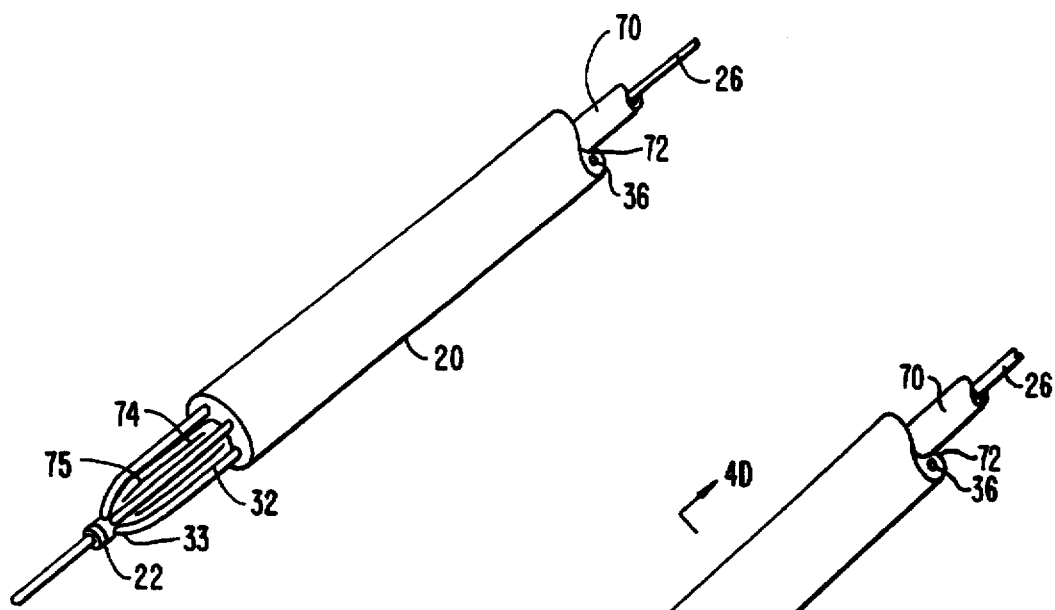
FIGS. 4A and 4B are perspective views of a further embodiment of an agent delivery catheter constructed in accordance with the principles of the present invention, showing the expansion member in the unexpanded and expanded configurations, respectively.
Figure 4B:
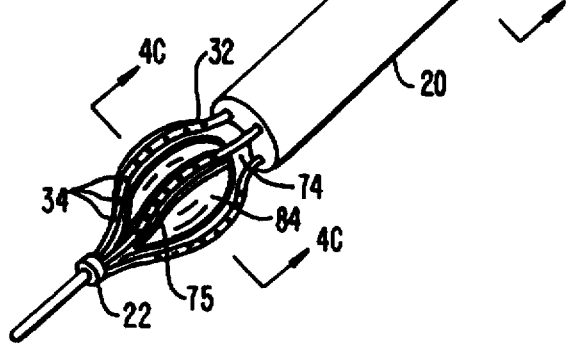
Figure 4C:
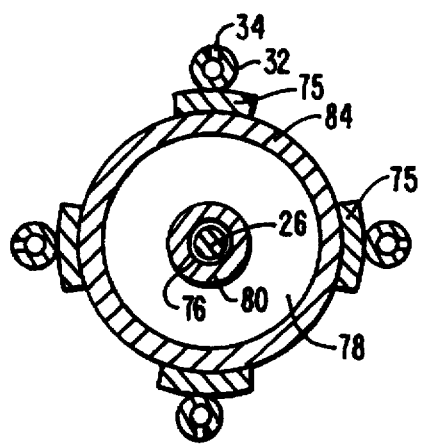
FIG. 4C is a transverse cross-section of a distal portion of the catheter of FIG. 4B.
Figure 4D:
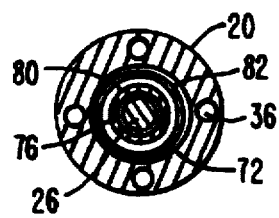
FIG. 4D is a transverse cross-section of the catheter shaft of the catheter of FIG. 4B.
Figure 4E:
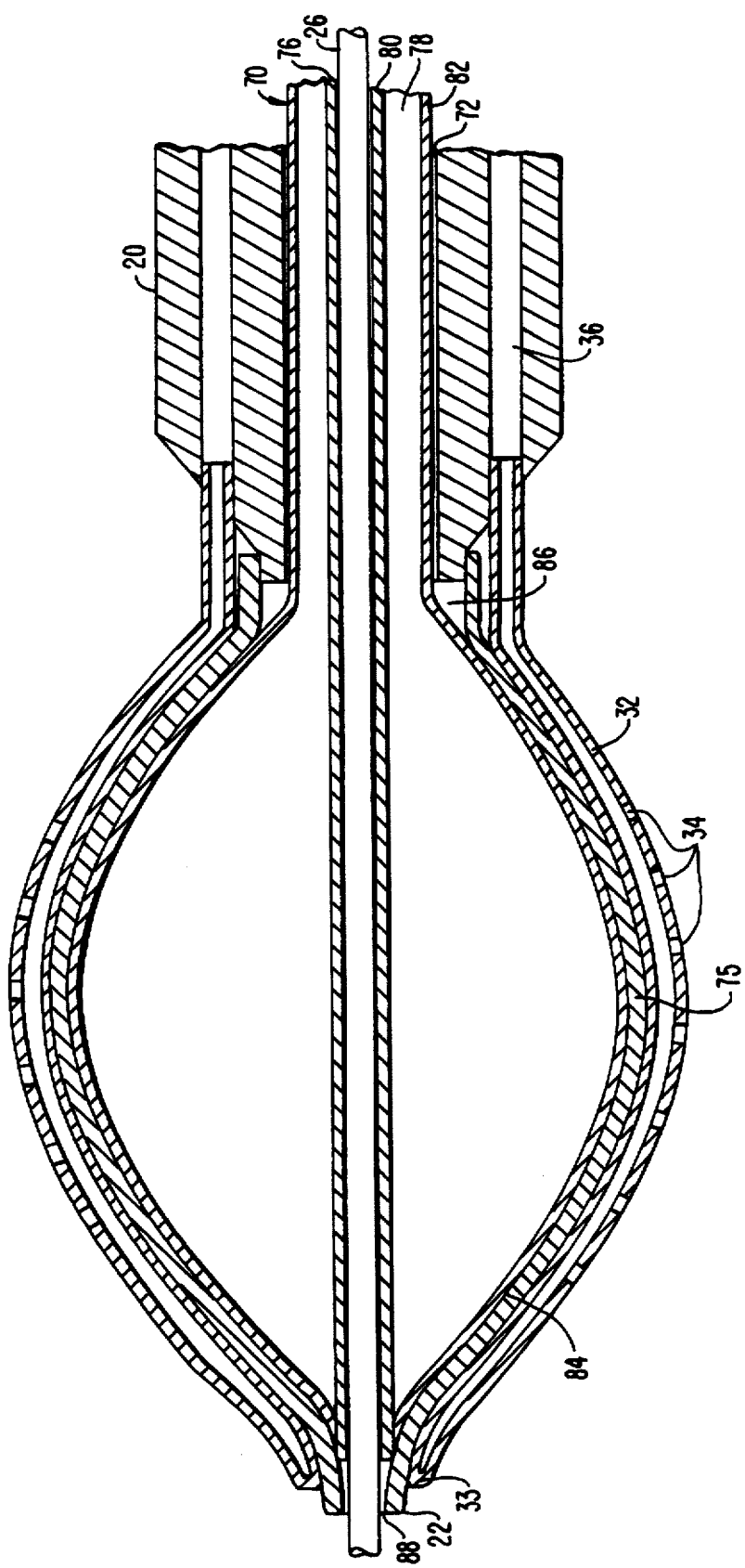
FIG. 4E is a longitudinal cross-section of the distal end of the catheter of FIG. 4B.

Removable dilatation catheter 70 is slidably disposed in axial passage 72 in catheter body 20. The dilatation catheter 70 will be of conventional construction, and includes a guidewire passage 76 in a core 80 as shown in FIG. 4D, through which guidewire 26 is slidably inserted. An outer casing 82 surrounds core 80, defining an inflation passage 78. An expansion member 84 is formed from, or adhesively mounted to the distal end of casing 82, and is sealed at distal end 22 about core 80. When dilatation catheter 70 is positioned in catheter body 20, expansion member 84 resides within interior lumen 86 of support member 74. Guidewire 26 and/or core member 80 extend distally through a distal opening 88 in support member 74.

Support member 74 will be constructed of a material similar to that of expansion member 84 so as to expand therewith. When expansion member 84 is inflated, as shown in FIGS. 4B and 4C, support sections 75 are distended and separated as they expand outward with the expansion member.

A further alternative embodiment of the catheter of the present invention is illustrated in FIG. 5. In this embodiment, the catheter comprises a plurality of delivery conduits 90 extending from the distal end 22 over expansion member 28 to the proximal end (not shown) of catheter shaft 20. Delivery conduits 90 have orifices 34 on a lateral surface thereof opposite expandable member 28. Delivery conduits 90 will be fastened at distal end 22 and to the exterior of catheter shaft 20, but will be unattached to expansion member 28. This permits delivery conduits 90 to be displaced as expansion member 28 is inflated, without creating stress concentrations on the surface of expansion member 28 as might be created by direct attachment of the conduits thereto. Furthermore, expansion member 28 may be compliant. Catheter shaft 20 and expansion member 28 will otherwise be substantially similar to those of FIGS. 1A–1E or 3A–3C. Delivery conduits 90 may be magifolded at the proximal end of the catheter as in the embodiment of FIGS. 1A–1E, or connected to separate agent introduction ports as in FIGS. 3A–3C for directional infusion. The invention as embodied in FIG. 5 provides a catheter of very simple, low-cost construction with independent infusion and expansion as well as directional infusion capabilities.

FIG. 6 illustrates a further embodiment of the catheter of the present invention. The catheter includes a body 20 having an expansion member 28 near its distal end 22, a guidewire lumen 44 extending through the body 20, and a plurality of delivery passages 36 integrated with body 20 in a longitudinal direction. In this embodiment, a proximal infusion array 30a is disposed on the catheter shaft proximal to expansion member 28, while a distal infusion array 30b is disposed on the catheter shaft distally of expansion member 28. Infusion arrays 30a, 30b include a plurality of orifices 34 disposed on a lateral surface of delivery conduits 32, which are in fluid connection with delivery passages 36. Distal portion of catheter body 20 distally of expansion member 28 may be of reduced diameter to facilitate positioning in a vessel. In this embodiment, the catheter of the present invention facilitates dilatation using expansion member 28, while infusing an agent through infusion arrays 30a, 30b. Infusion may be performed independently of dilatation, permitting infusion of the agent before, during, after, or without dilatation. Further, as in other embodiments, each delivery passage 36 and delivery conduit 32 combination is independent of each other, so as to facilitate directional infusion and/or infusion of two or more different agents simultaneously. It is also understood that the catheter may include only one of either distal infusion array 30b or proximal infusion array 30a, and that orifices 34 may be included only on selected ones of delivery conduits 32. Further, the catheter may comprise, in addition to infusion arrays 30a and/or 30b, an infusion array about the periphery of the expansion member in the manner described above with reference to FIGS. 1-3.

Catheters constructed in accordance with the principles of the present invention may optionally be modified to provide for perfusion or by-pass blood flow, as generally described in U.S. Pat. Nos. 4,661,094, and 4,892,519, the disclosures of which are incorporated herein by reference. Generally, such perfusion flow can be provided by one or a series of perfusion ports on the proximal side of the expansion member 28, which ports permit the flow of blood into the shaft core 46 and eventually out through the distal opening of said core. In this way, blood flow can be maintained even when the expansion member 28 is expanded and would (in the absence of the perfusion capability) block blood flow.

It should be understood that the catheter of the present invention is suitable for delivery of a variety of therapeutic agents including pharmaceuticals, proteins, peptides, nucleotides, carbohydrates, polysaccharides, muccopolysaccharides, simple sugars, glycosaminoglycans and steroids. The present invention facilitates delivery of such agents in a variety of formulations, including aqueous vehicle or liposome. The drug delivery catheter is further useful for delivery of viral particles to facilitate gene transfer. The agents delivered may perform a variety of functions, including antithrombotics, antiplatelets, antimetabolics, growth factor inhibitors, growth promoters, anticoagulants, antimitotics, and antibiotics.

In a further embodiment, illustrated in FIGS. 9–17, the agent infusion catheter is configured to slidably receive a conventional dilatation catheter within an axial guide passage in the infusion catheter shaft. This allows the dilatation catheter to serve as a guide wire for the infusion catheter to guide the catheter to the treatment site, facilitates dilatation of a stenotic vessel independently of agent infusion, and permits the use of any of a variety of commercially-available dilatation catheters in conjunction with the agent infusion catheter of the invention. Dilatation catheters suitable for use with the infusion catheter illustrated in FIGS. 9–17 are described, for example, in U.S. Pat. No. 5,041,089, U.S. Pat. No. 4,323,071, U.S. Pat. No. 4,292,974, U.S. Pat. No. 4,762,129 and U.S. Pat. No. 4,775,371, the complete disclosures of which are incorporated herein by reference. Such dilatation catheters are commercially available from, for example, Advanced Cardiovascular Systems, Inc., of Santa Clara, Calif.

Figure 9:
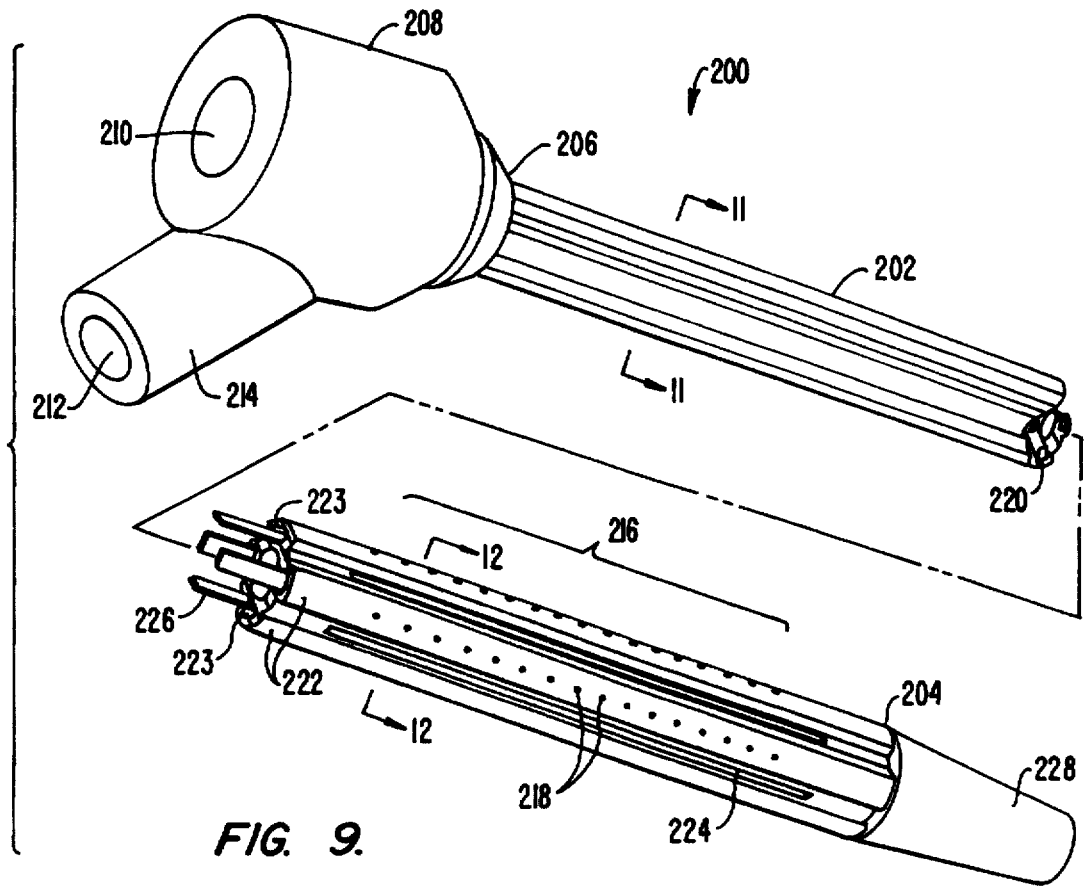
FIG. 9 is a perspective view of a further embodiment of an agent delivery catheter constructed in accordance with the principles of the invention.

Referring to FIG. 9, in a preferred embodiment, agent infusion catheter 200 includes an elongate flexible shaft 202 having a distal end 204 and a proximal end 206. A manifold assembly 208 is fixed to the proximal end of the shaft and includes dilatation catheter port 210 on its proximal end and an agent introduction port 212 in a fitting 214 provided with a Luer lock (not shown), secured to the assembly. At the distal end of the shaft 202 is an infusion array 216 having a plurality of orifices 218 along lateral surfaces of the shaft. Shaft 202 comprises a plurality of axially disposed agent delivery passages 220 extending from the proximal end which are connected to a corresponding number of agent delivery conduits 222 at the distal end. Orifices 218 are in communication with interior axial lumens 233 in delivery conduits 222. An axial cut or slot 224 is formed in shaft 202 between each of delivery conduits 222 such that the delivery conduits are separated from one another by the slots. A stiffening element 226 is disposed in at least a single delivery conduit 222, as described more fully below. A conically tapered distal tip 228 is fixed to the distal end 204 of the shaft.

In a preferred embodiment, shaft 202 will be constructed of materials and will have dimensions selected as appropriate for insertion of the shaft transluminally inside a guiding catheter (not shown), in a blood vessel. In an exemplary embodiment, shaft 202 will have a length in the range of 110 to 150 cm, and an outer diameter of 1.1 mm–2.3 mm (0.04 to 0.09 inches). Infusion array 216 will be approximately 10 to 60 mm in length. Catheter shaft 202 may be any of a variety of biocompatible, flexible materials including, for example, polyester, polyethylene or polyamide. Preferably, as described above, catheter shaft 202 (including delivery passages 220) and delivery conduits 222 will comprise a single, monolithic extrusion from proximal end 206 to distal end 204.

As shown in FIG. 10A, in an undeployed configuration, infusion array 216 is aligned with and has an outer diameter generally equal to that of the proximal portion of shaft 202. As shown in FIG. 10B, a dilatation catheter 230 may be positioned through an axial guide passage of shaft 202 (described below) such that a balloon or other expansion member 232 at the distal end of the dilatation catheter is within infusion array 216 adjacent delivery conduits 222. By expanding balloon 232, infusion array 216 is deployed radially outward to bring orifices 218 adjacent to a treatment site on a vessel wall.

Figure 11:
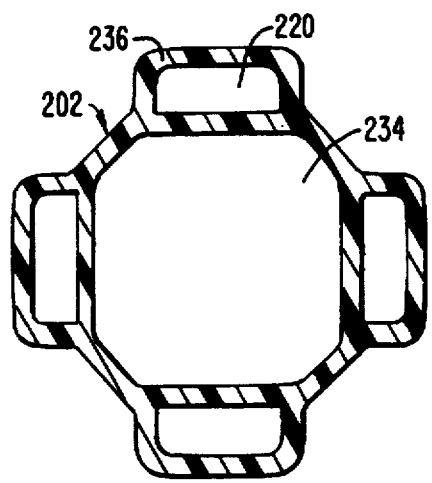
FIG. 11 is a transverse cross-section through line 11—11 in a proximal portion of the shaft of the catheter of FIG. 9.

FIG. 11 illustrates a transverse cross-section through a proximal portion of shaft 202. A guide passage 234 extends longitudinally through the catheter shaft for slidably receiving a dilatation catheter. Guide passage 234 may be coated with a lubricous material such as a hydrogel or fluorocarbon polymer, for example, fluorinated ethylenepropylene or polytetrafluoroethylene, available commercially under the trademark Teflon® from DuPont. Such a coating facilitates longitudinal positioning and-alignment of a dilatation catheter in guide passage 234 when catheter 200 is disposed in a tortuous configuration in a vessel. Guide passage 234 will have a diameter of 0.7–2.0 mm (0.03–0.08 inches), preferably 1.2–1.8 mm (0.05–0.07 inches), suitable for receiving most commercially-available dilatation catheters in current use.

Delivery passages 220 run parallel to guide passage 234. In an exemplary embodiment, delivery passages 220 are disposed in longitudinal ribs 236 which protrude radially outward from shaft 202. Delivery passages 220 will have an interior height (or diameter, if round) in the range of 0.01 mm to 0.7 mm (0.005–0.03 inches).

Figure 12A:
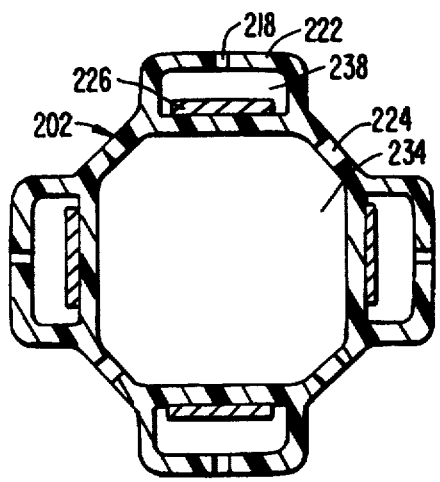
FIGS. 12A–12E are transverse cross-sections through line 12—12 at the distal end of the shaft in the catheter of FIG. 9 illustrating various embodiments of the stiffening elements in the infusion array.

FIGS. 12A–12E illustrate transverse cross-sections of the distal portion of shaft 202 through infusion array 216 in Various embodiments. In the embodiment of FIG. 12A, delivery conduits 222 are separated from each other by slots 224 so as to permit lateral expansion for deployment of the delivery conduits. Delivery conduits 222 have an axial lumen 238 which is in communication with delivery passages 220 in the catheter shaft. Delivery conduits 222 surround guide passage 234. Stiffening elements 226 are disposed within axial lumen 238 and occupy only a portion thereof to permit flow of agent through the lumen. In the embodiment of FIG. 12A, stiffener elements 226 comprise ribbon or bar-shaped rods of generally rectangular cross-section. The rods may be unrestrained in the axial lumens of the delivery conduits, secured at their distal end to the distal tip as described below, or co-extruded in the walls of the delivery conduits, also described below. Stiffener elements 226 may be any of a variety of materials such as stainless steel, tantalum, nickel-titanium, or tungsten and having a geometrical configuration leading to greater axial rigidity but being laterally more flexible and resilient. The stiffening elements may extend from distal end 204 to proximal end 206 of shaft 202 through the delivery passages, or may have a shorter length. e.g. 30–70 mm, so as to extend from a point near distal end 204 to a point just proximal to infusion array 216.

Stiffener elements 226 serve several functions. First, the stiffener elements help to maintain the patency of axial lumens 238 in the delivery conduits. Second, stiffener elements 226 provide stiffness and resilience to delivery conduits 222 such that, following expansion of the delivery conduits, they will recoil back to the undeployed configuration. Third, stiffener elements 226 serve to maintain the relative alignment between the delivery conduits during longitudinal positioning and later expansion, so that the delivery conduits remain approximately equally separated from each other when deployed, facilitating uniform treatment of an area of the vessel wall. Furthermore, a stiffener element 226 of rectangular cross-section allows controlling the relative magnitude of lateral versus radial stiffness. In the configuration shown, the bending stiffness of stiffener element 226 is substantially less in the radial direction about a first axis perpendicular to the shaft than in the lateral direction about a second axis perpendicular to the shaft and perpendicular to the first axis.

Figure 12B:
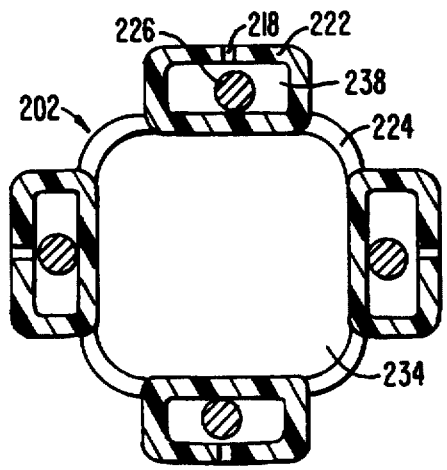

FIG. 12B illustrates a further embodiment of delivery conduits 222 and stiffening elements 226. In this embodiment, slot 224 is significantly wider than in previous embodiments, such that substantially all of the material between delivery conduits 222 is removed. Further, in this embodiment, stiffener elements 226 comprise rods having a round cross-section. With such a shape, the stiffener elements are particularly effective in maintaining the patency of axial lumen 238. Further, the stiffener elements of round cross-section will not tend to block passage of an agent through orifices 218 if the rods float to the outer surface of the axial lumen.

Figure 12C:
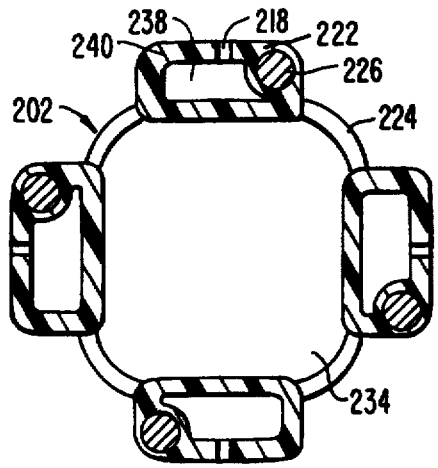

In the embodiment of FIG. 12C, stiffener elements 226 comprise rods round in cross-section embedded in the outer wall 240 of delivery conduit 222. It should be understood that stiffener elements of various cross-sectional shapes may be embedded in the wall of the delivery conduits in the manner shown in FIG. 12C.

Figure 12D:
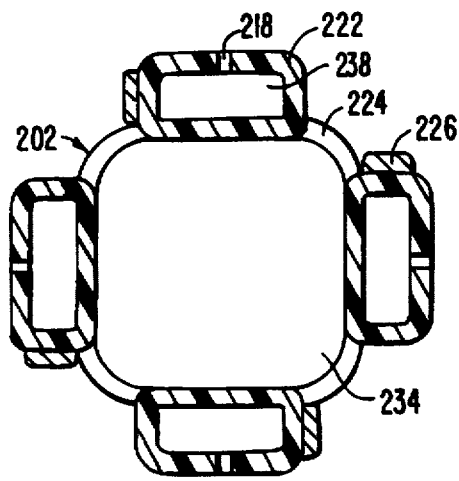

In the embodiment of FIG. 12D, stiffener elements 226 are disposed exterior to delivery conduits 222. In an exemplary embodiment, the stiffener elements are disposed along a side surface of each delivery conduit so as not to interfere with contact between the outer lateral surfaces of the delivery conduits and the wall of the vessel. Again, stiffener elements of various configurations may be used, including round, rectangular, and other cross-sectional shapes.

Figure 12E:
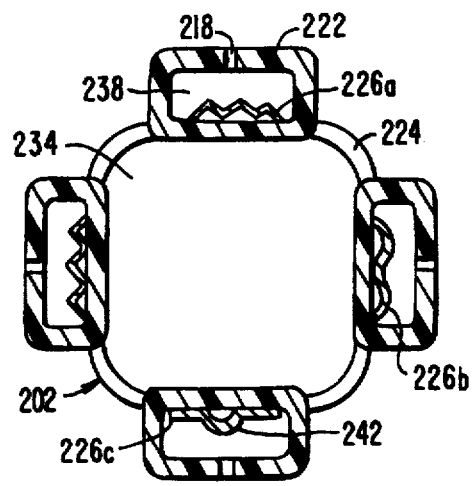

In FIG. 12E, several additional embodiments of stiffener elements 226 are illustrated. In these embodiments, the stiffener elements have a surface contour which prevents the stiffener elements from blocking flow of agent through orifices 218 should the stiffener elements float outward against the outer wall of the axial lumen. In one embodiment, stiffener element 226a has a zig-zag cross-section. In a second embodiment, stiffener element 226b has a double curve or wave cross-section. In a third embodiment, stiffener element 226c has a longitudinal ridge 242. In these embodiments, a plurality of transverse slots (not shown) may be provided at various points along the length of the stiffener elements to reduce radial stiffness and enhance the free flow of agent from one side of the stiffener element to the other.

In another exemplary embodiment, illustrated in FIG. 12F, stiffener elements 226 will have a plurality of cut-outs 227 along their length, which may take the form of indentations along the longitudinal edges as shown, or, alternatively, slots or holes through a middle portion of the stiffener elements. Cut outs 227 facilitate flow of agent from one side of the stiffener elements to the other to ensure the agent is not blocked from flowing through orifices 218.

In a further embodiment of infusion array 216, illustrated in FIGS. 13 and 14A, an elastomeric sleeve 248 is mounted in guide passage 234, with delivery conduits 222 disposed about the periphery of the elastomeric sleeve. Elastomeric sleeve 248 will comprise a tubular element of a flexible and resilient elastomeric polymer, such as silicon or urethane. Usually, delivery conduits 222 will be fixed to the exterior of elastomeric sleeve 248. In this way, the elastomeric sleeve serves to facilitate resilient return of the delivery conduits from the deployed to the undeployed position. In addition, the elastomeric sleeve serves to maintain alignment of the delivery conduits as they are expanded so as to maintain proper spacing between adjacent delivery conduits. While stiffener elements 226 are included in FIGS. 13 and 14, the use of elastomeric sleeve 248 may obviate the need for stiffening elements, as the sleeve may adequately maintain alignment and provide resilience.

In an alternative embodiment, illustrated in FIG. 14B, elastomeric sleeve 248 is disposed external to delivery conduits 222, with the delivery conduits secured to the interior of the sleeve. Orifices 218 extend from axial lumen 238 through delivery conduits 222 as well as through elastomeric sleeve 248. In a preferred embodiment, the elastomeric sleeve is configured so as to generally conform to the exterior contour of the delivery conduits, minimizing the profile of the distal portion of the catheter, as well as accommodating the expansion of the delivery conduits.

Figure 15A:
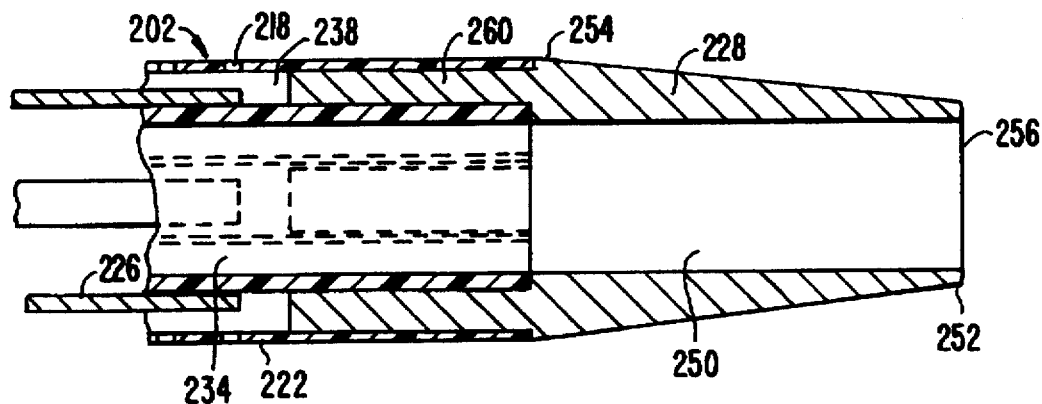
FIGS. 15A–15B are a side cross-section and a perspective view, respectively, of the distal tip of the catheter of FIG. 9.
Figure 15B:
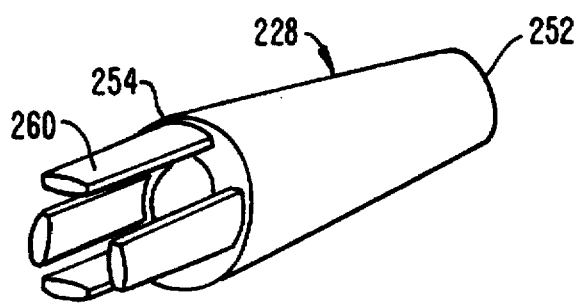
Figure 15C:
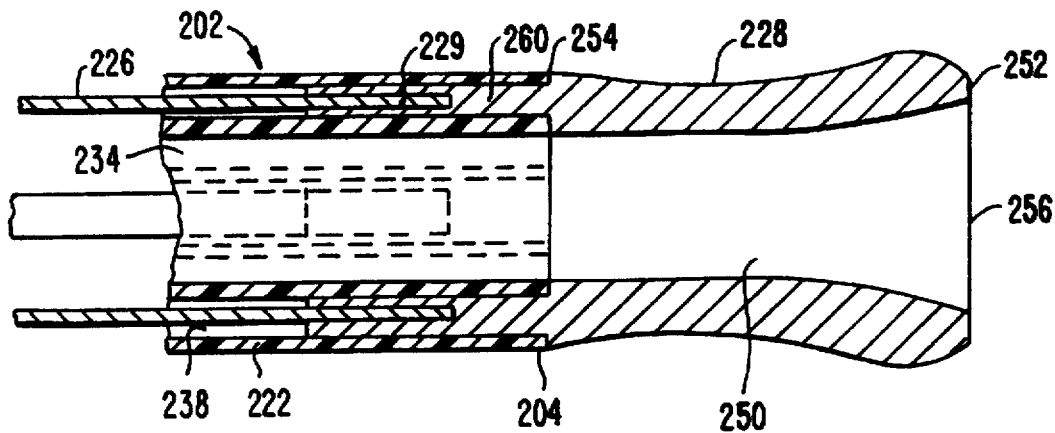
FIG. 15C is a side cross-sectional view of a further embodiment of a distal tip constructed in accordance with the principles of the invention.

Referring now to FIGS. 15A–15C, distal tip 228 will be more fully described. Distal tip 228 provides a minimally traumatic leading edge to catheter 200, as well as facilitates slidable tracking of catheter 200 over a dilatation catheter, as described more fully below. In addition, the distal tip 228 provides a seal for the distal ends of delivery conduits 222.

In an exemplary embodiment, shown in FIGS. 15A–15B, distal tip 228 has an axial passage 250 aligned with guide passage 234 in shaft 202. Distal tip 228 has a conically tapered exterior to enhance navigation of the catheter through a vessel lumen. Usually, distal tip 228 will have a length of 1 to 5 mm and exterior diameter at proximal end 254 generally equal to that of the outer surface of the delivery conduits 222, with distal end 252 being approximately 30% smaller in diameter than proximal end 254. Distal tip 228 further includes a plurality of proximally-extending prongs 260, which fit within axial lumens 238 at the distal ends of delivery conduits 222. Prongs 260 thereby provide a seal for the distal end of the delivery conduits and provide the adhesion to shaft 202 required to properly retain distal tip 228 with the catheter. Prongs 260 can also be employed to retain the distal ends of stiffener elements 226 within axial lumens 238. In one embodiment, distal tip 228 may be molded urethane, formed by a process in which urethane is poured into a mold and the distal end of shaft 202 is inserted into the mold while the urethane is liquid, permitting the urethane to wick into axial lumens 238, thereby forming prongs 260.

In an alternative embodiment of the distal tip, illustrated in FIG. 15C, distal tip 228 has a trumpet shape wherein axial passage 250 tapers radially outward in the distal direction. The outer periphery of distal tip 228 may be tapered inward near the distal end 252 to facilitate navigation through a vessel lumen. The trumpet-shaped distal tip of FIG. 15C facilitates smooth retraction of the expansion member (e.g. balloon) of a dilatation catheter from a position distal to distal tip 228 to a position within guide passage 234 adjacent delivery conduits 222.

FIG. 15C further illustrates the retention of distal ends 229 of stiffener elements 226 by encapsulation in prongs 260 of the distal tip. In this embodiment, when distal tip 228 is to be formed, stiffener elements 226 are positioned in axial lumens 238 of the delivery conduits with distal ends 229 near the distal end 204 of shaft 202. Distal tip 228 is then formed as described above, by pouring a polymer such as urethane into a mold and putting the distal end of the catheter shaft in the mold while the urethane is liquid. The urethane then wicks into axial lumens 234, encapsulating the distal ends of the stiffener elements.

Figure 16:
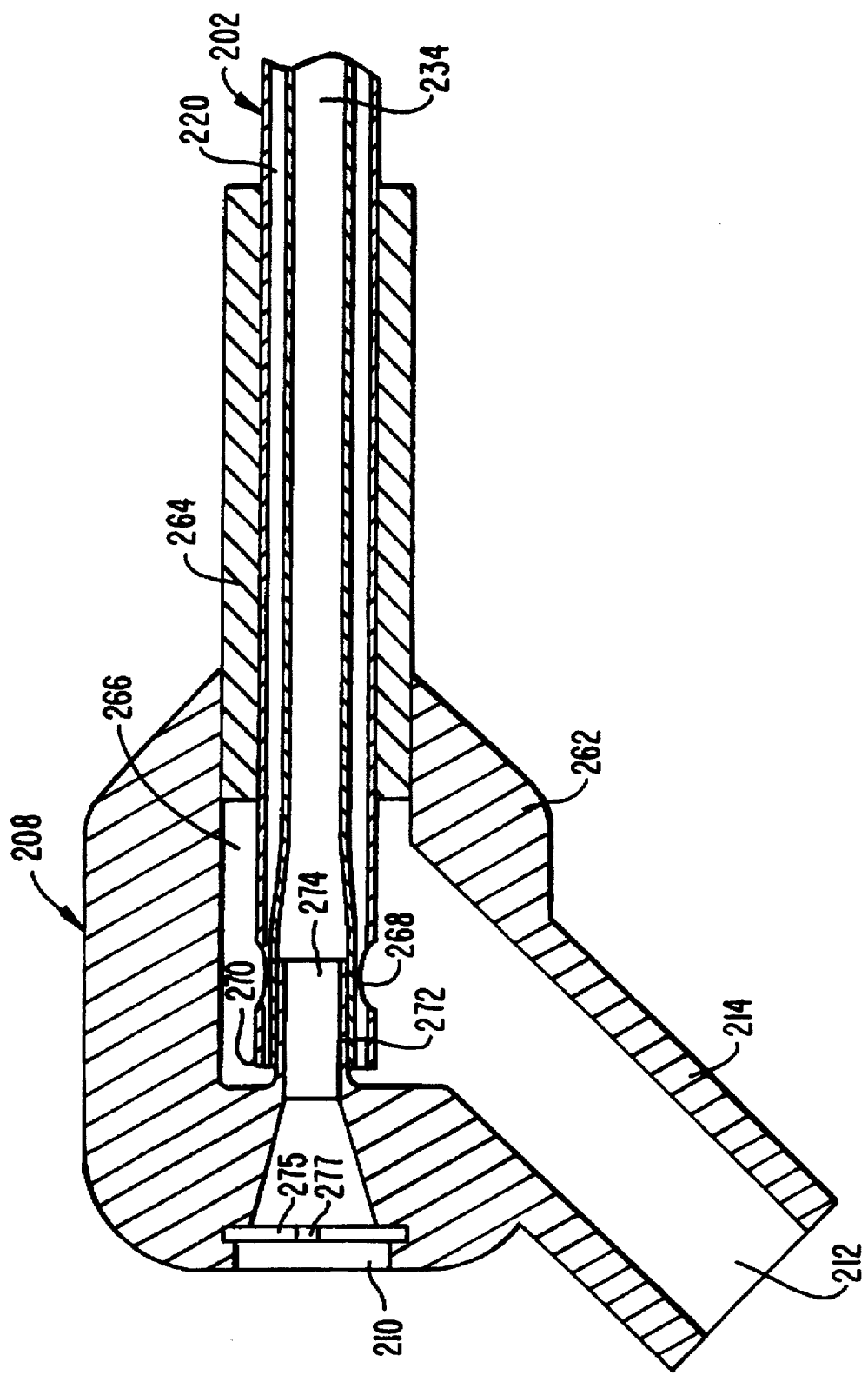
FIG. 16 is a side cross-section of the manifold assembly at the proximal end of the catheter of FIG. 9.

Referring now to FIG. 16, manifold assembly 208 will be more fully described. The manifold assembly includes a housing 262 which may be a metal or any of a variety of rigid plastics, including acrylonitrile-butadiene-styrene (ABS), Delrin®, polycarbonate and the like. Shaft 202 extends through a flexible polymeric strain relief 264 into an interior chamber 266 within housing 262. The proximal end 270 of shaft 202 is secured about a cylindrical mandrel 272 formed in housing 262. Mandrel 272 has an axial bore 274 which connects dilatation catheter port 210 to guide passage 234. In a preferred embodiment, a diaphragm 275 is mounted in a proximal portion of bore 274 near catheter port 210. Diaphragm 275 has a passage 277 which may comprise a hole or slit which elastically expands when a dilatation catheter of larger diameter is inserted through it. The diaphragm thus provides a sealed entrance for, introducing a dilatation catheter into guide passage 234.

Chamber 266 is in communication with agent introduction port 212 in Luer fitting 214. The proximal end of shaft 202 will have circumferential notches 268 providing fluid communication between chamber 266 and agent delivery passages 220. Luer fitting 214 will be configured for connection to a precision agent delivery device. In this way, an agent delivered through delivery port 212 will flow into delivery passages 220 for delivery to infusion array 216.

Figure 8A:
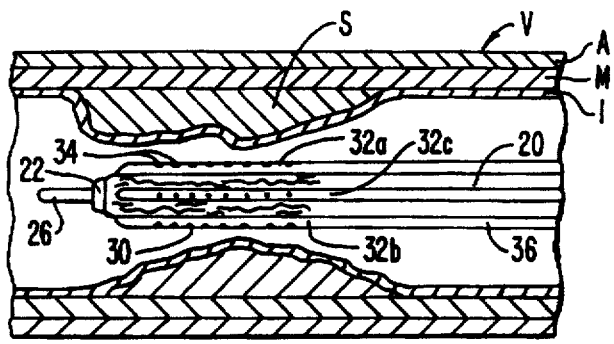
FIGS. 8A and 8B are side views of the catheter of FIG. 1 positioned within a body lumen according to the principles of the method of the present invention.
Figure 8B:
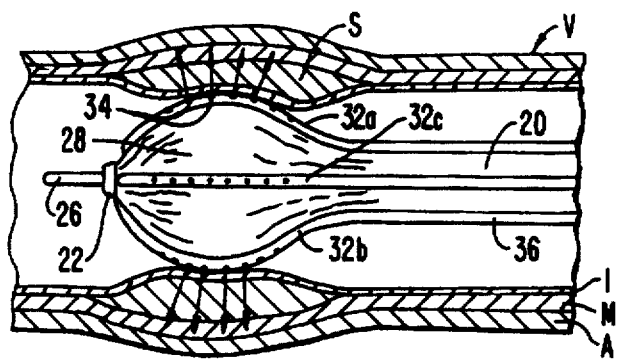

In a preferred embodiment of the method of the present invention, illustrated in FIGS. 8A and 8B, the catheter is positioned transluminally in a body lumen or vessel V, which will typically be an artery. The vessel will have a wall comprising three layers, including intima I, media M and adventitia A. The catheter will be positioned such that orifices 34 in delivery conduits 32 are disposed near the treatment site, which will most often be an atherosclerotic region of stenosis S in the artery. Usually, a movable guide wire 26 will be used to guide the catheter through the artery. A fixed guidewire attached to the distal end 22 of the catheter may be used instead.

When the catheter has been positioned near the treatment site S, the expansion member 28 is inflated with an inflation fluid introduced through inflation fluid introduction port 42 in housing 38 at the proximal end of the catheter. Preferably, expansion member 28 is expanded sufficiently to bring delivery conduits 32 into contact with the treatment site S. If desired, dilatation of the vessel may be performed by inflating expansion member 28 sufficiently to expand the interior of the vessel lumen in the region of stenosis so as to effectively restore blood flow to an appropriate level.

Frequently, it will be desirable to impregnate the treatment site S with an agent before, during or after such dilatation. Advantageously, the physician may position the delivery conduits 32 against the treatment site and perform any desired dilatation without infusing any agent through orifices 34 in conduits 32. When agent delivery is desired, an agent is introduced through agent introduction port 40 in proximal housing 38, from which it is communicated through delivery passages 36 to delivery conduits 32. The agent will be infused through orifices 34 to penetrate the treatment site S. Usually, the agent will be infused into the treatment site at pressures sufficient to attain penetration to at least the media M, and preferably into the adventitia A of the vessel.

In an alternative method, an agent may be infused into the lumen before expanding the expansion member. After infusion, or while it is continuing, an inflation fluid may be introduced into the device to expand the expansion member, positioning the delivery conduits adjacent the lumen wall. Infusion of the agent may continue, or a different agent may be infused through the delivery conduits to penetrate a treatment site within the lumen wall.

In a specific embodiment, the method may comprise infusing an agent through one or more selected delivery conduits 32 without infusing the agent through other selected delivery conduits. Using the catheter illustrated in FIGS. 3A–3C, the agent will be introduced through one or more agent introduction ports 140 connected to the delivery conduits 32 which are to be used for infusion. For example, in FIGS. 8A and 8B, an agent may be infused through delivery conduits 32a, 32b, but not through delivery conduit 32c, by introducing the agent through the corresponding introduction ports 140 at the proximal end of the catheter.

In a further embodiment, the method may include infusing a first agent through selected ones of delivery conduits 32 while infusing one or more different agents through others of delivery conduits 32. Referring to FIGS. 8A and 8B, a first agent, such as a growth inhibitor, may be infused through delivery conduit 32c, while infusing a second agent, such as an anticoagulant, through delivery conduits 32a, 32b. This is accomplished by introducing the first agent through the appropriate introduction port 140 (FIG. 3A) connected to conduits 32a, 32b, while introducing the second agent through the introduction port 140 connected to delivery conduit 32c.

Once treatment at a particular site has been completed, drug delivery may be terminated, and, if desired, expansion member 28 deflated by withdrawing the expansion fluid through inflation passage 54. Dilatation and/or agent infusion may be repeated at the treatment site S. When treatment of the site is complete, the catheter may be repositioned without removing it from the body to perform dilatation and/or agent infusion at a new treatment site. It can be seen that the device and method of the present invention facilitate infusion of an agent with or without dilatation, dilatation with or without infusion, infusion of multiple agents simultaneously, directional infusion, and treatment of multiple sites, without removing the device from the body between such treatments.

A further embodiment of the method of the invention is illustrated in FIGS. 17A–17D. In this embodiment, utilizing the agent infusion catheter 200 described above in connection with FIGS. 9–16, a balloon dilatation catheter DC of conventional construction is transluminally positioned in a blood vessel V such that a balloon or other expansion member 280 (in an uninflated configuration) is near a treatment site S. Typically, dilatation catheter DC will be positioned over a movable flexible guide wire GW. During this step, agent infusion catheter 200 need not be, but may be, positioned slidably over dilatation catheter DC. In some embodiments, it would be desirable to position a dilatation catheter in the vessel first, do a dilatation and then remove the dilatation catheter. Subsequently, catheter 200 is introduced over the dilatation catheter and both catheters are introduced together into the vessel. In other instances, catheter 200 will be positioned over the dilatation catheter outside of the body, and both catheters will be transluminally positioned in the vessel together. The dilatation catheter may then be used to perform dilatation as described below.

Figure 17A:
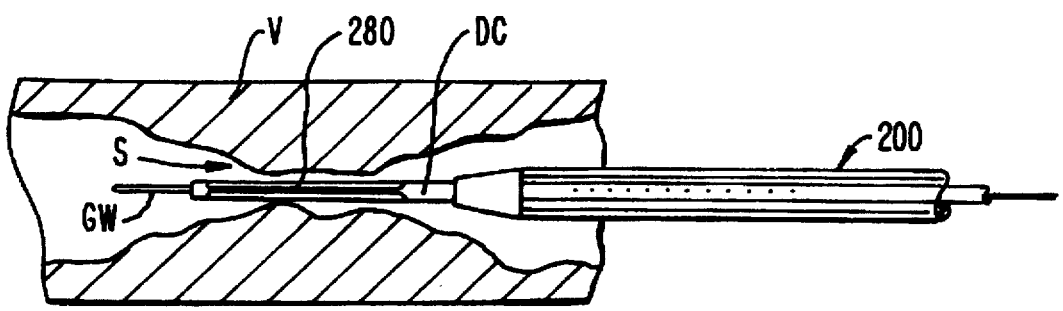
FIGS. 17A–17D are side views illustrating the catheter of FIG. 9 positioned in a body lumen according to the method of the invention.
Figure 17B:
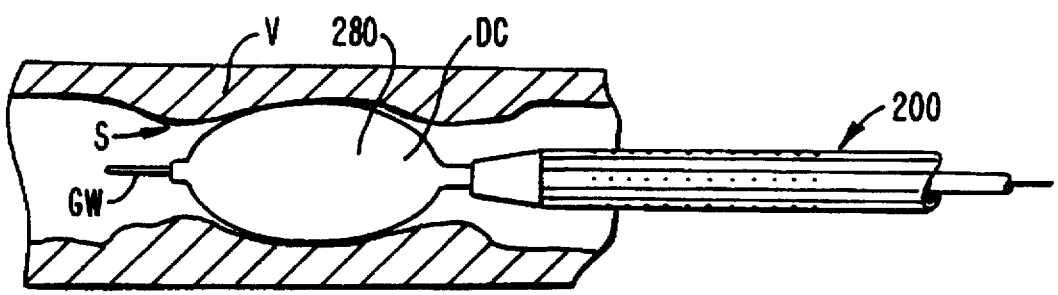

As shown in FIG. 17B, balloon dilatation catheter DC is positioned such that expansion member 280 is disposed distal to the distal end of agent infusion catheter 200. Expansion member 280 is then inflated using known techniques, dilatating vessel V at treatment site S.

Figure 17C:
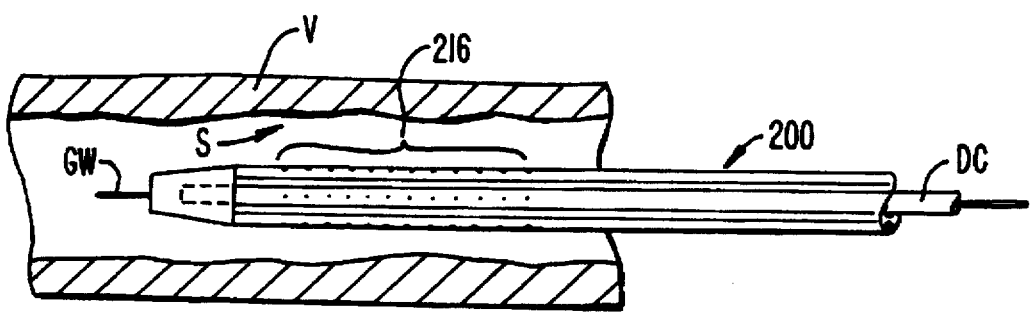
Figure 17D:
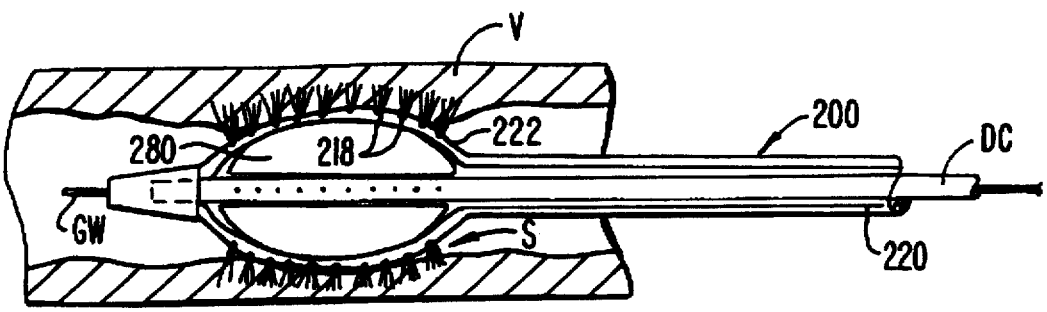

Expansion member 280 is then deflated and, as shown in FIG. 17C, dilatation catheter DC is drawn proximally relative to agent infusion catheter 200. Dilatation catheter DC is positioned such that expansion member 280 is adjacent infusion array 216 in the interior guide passage of catheter 200, described above. Agent infusion catheter 200 is then positioned within vessel V such that infusion array 216 is near treatment site S.

Expansion member 280 is then inflated so as to position delivery conduits 222 in apposition to treatment site S on the vessel wall. An agent is then delivered through delivery passages 220 in catheter 200 to delivery conduits 222. The agent is infused under pressure through the delivery conduits and through orifices 218 to penetrate the vessel wall in the region of treatment site S. When treatment is complete at the site, agent delivery is discontinued, and expansion member 280 deflated to return delivery conduits 222 to an undeployed position as in FIG. 17C. If further treatment is desired at the same or different site, dilatation catheter DC may be extended distal to infusion catheter 200 to the position shown in FIG. 17A. Dilatation and/or agent infusion may be repeated at the same or a different site.

To facilitate longitudinal positioning of infusion catheter 200 in a vessel lumen, as well as to assist proper axial alignment of the expansion member (e.g. balloon) of the dilatation catheter with infusion array 216, radiopaque markers may be provided on infusion catheter 200. In a preferred embodiment, shown in FIGS. 18A–18C, radiopaque markers 282 are disposed on one or more of stiffener elements 226. Markers 282 are formed by, for example, plating a radiopaque material such as gold or platinum onto stiffener elements 226. Dilatation catheter DC will also have a radiopaque marker 284, which is typically formed on the inner shaft 286 of catheter DC in the interior of expansion element 280. In one embodiment, shown in FIG. 18A, at least two markers 282 are disposed on stiffener elements 226 in a central portion of infusion array 216, the markers being separated a distance from one another usually about equal to or slightly greater than the length of marker 284 on dilatation catheter DC. In this way, by visualization through a radiographic imaging device, markers 282 facilitate axial alignment of expansion element 280 with infusion array 216 by aligning dilatation catheter marker 284 between markers 282 on stiffener elements 226. Markers 282 further provide visual indication of the location of infusion catheter 200 within the vessel so that infusion array 216 may be positioned adjacent to a treatment site.

Alternative embodiments of radiopaque markers 282 are illustrated in FIGS. 18B and 18C. In FIG. 18B, marker 282 is disposed on a distal portion of stiffener element 226. In this way, dilatation catheter DC and/or infusion catheter 200 are axially re-positioned relative to one another until marker 284 on the dilatation catheter is exposed on the proximal side of marker 282. In the embodiment of FIG. 18C, marker 282 is disposed on a proximal portion of stiffener element 226 whereby the catheters are axially aligned by positioning dilatation catheter marker 284 distal to marker 282 on the stiffener element.

An alternative infusion array 300 is illustrated in FIGS. 19 and 20. The infusion array 300 is connected to the end of a flexible shaft (not shown) and is similar in certain respects to that illustrated in FIGS. 9, 10A, and 10B, described above. The array 300 includes four isolated drug delivery conduits 302, and the delivery conduits 302 will be connected to delivery passages on the proximal shaft in a manner similar to that of the catheter of FIGS. 9, 10A, and 10B. The delivery conduits 302 are formed on or as part of a sleeve, with web portions 303 of the sleeve between adjacent pairs of conduits 302 being axially split to facilitate expansion by an internal balloon 304 at the distal end of a balloon catheter 306. The sleeve will usually be inelastic, typically being formed from any of the materials described above for the shaft 202 of infusion catheter 200. The web of the sleeve may be split by cutting along a single line (and not removing material) or by cutting along parallel lines and removing material to form slots. The infusion array 300 differs from that illustrated in FIGS. 9, 10A, and 10B in the pattern of splits which is formed between adjacent pairs of conduits 302. As best seen in FIG. 20 (which is a planar projection of the sleeve of infusion array 300), a first pair of opposed web portions 303a will have a single split 310 which extends over most or all of the length of the sleeve of the infusion array. A second opposed pair of web portions 303b, in contrast, will be only partially split, having two axially spaced-apart splits 312 and 314. In a particularly preferred embodiment, the splits 312 and 314 will not be aligned, i.e., non-split regions 316 and 318 will not overlap each other.

As observed in FIG. 19, the pattern of splits 310, 312, and 314 provides a relatively uniform and repeatable circumferential distribution of the delivery conduits 302 along the entire length of the sleeve of infusion array 300. This is in contrast to the design of FIG. 10B, where an infusion array which is fully split between adjacent delivery conduits may result in a less uniform circumferential distribution of the delivery conduits which may bunch together at localized regions on the infusion array. Such a non-uniform delivery conduit distribution is not always optimum for drug delivery. By controlling the pattern of axial splits between adjacent conduits, other more repeatable conduit distributions can be achieved. The pattern of FIGS. 19 and 20 provides a particularly uniform distribution of the conduits over most of the length of the infusion array.

While the above is a complete description of the preferred embodiments of the invention, various alternatives, modifications, and equivalents may be used. Therefore, the above description should not be taken as limiting the scope of the invention which is defined by the appended claims.

What is claimed is:

1. Apparatus for infusing an agent to a treatment site on a wall of a body lumen, the apparatus comprising:
   a flexible shaft having a distal end, a proximal end and first and second passages therebetween;
   an expansion member disposed at the distal end of the shaft, the interior of the expansion member being in fluid communication with the first passage;
   at least one laterally-deflectable delivery conduit secured at the distal end of the shaft adjacent the expansion member, the delivery conduit having a plurality of orifices on a lateral surface thereof and an axial lumen connecting the orifices to the second passage in the shaft; and
   an axially rigid stiffening element disposed axially in the delivery conduit.

2. The apparatus of claim 1 wherein the stiffening element comprises a rod embedded in a wall of the delivery conduit.

3. The apparatus of claim 1 wherein the stiffening element comprises a rod disposed in the axial lumen of the delivery conduit.

4. The apparatus of claim 1 wherein the stiffening element comprises a rod fixed to the exterior of the delivery conduit.

5. The apparatus of claim 1 wherein the stiffening element is a resilient metal.

6. The apparatus of claim 1 wherein at least a portion of the stiffening element is radiopaque.

7. The apparatus of claim 6 further comprising a radiopaque marker fixed to the expansion member, the radiopaque portion of the stiffening element being disposed in a position selected to facilitate alignment of the expansion member adjacent to the delivery conduit by positioning the radiopaque marker relative to the radiopaque portion of the stiffening element.

8. The apparatus of claim 1 further comprising:
   a guide passage between the proximal and distal ends of the shaft; and
   an inflation tube slidably disposed in the guide passage, the inflation tube having a proximal end and a distal end, wherein an inflation lumen is disposed in the inflation tube and the expansion element is secured to the distal end of the inflation tube.

9. The apparatus of claim 8 wherein the guide passage has an open distal end such that the expansion member may be advanced distally from the distal end of the shaft.

10. The apparatus of claim 1 further comprising a plurality of said delivery conduits arranged about the distal end of the shaft.

11. The apparatus of claim 10 further comprising means attached to the apparatus for maintaining alignment of the delivery conduits during deflection thereof.

12. The apparatus of claim 11 wherein the means for maintaining alignment comprises a tubular sleeve, wherein the delivery conduits are disposed on or in a surface of the sleeve.

13. The apparatus of claim 12 wherein the sleeve is disposed interior to the delivery conduits, the delivery conduits being secured to an exterior surface of the sleeve.

14. The apparatus of claim 12 wherein the sleeve is disposed exterior to the delivery conduits, the delivery conduits being secured to an interior surface of the sleeve, wherein the orifices extend from the axial lumens of the delivery conduits through the sleeve.

15. The apparatus of claim 10 further comprising a plurality of independent delivery passages from the proximal end to the distal end of the shaft, at least a first of the delivery conduits being connected to a different delivery passage than a second of the delivery conduits so as to allow independent delivery of agents through the first and second delivery conduits.

16. The apparatus of claim 1 wherein the shaft and delivery conduits comprise a single monolithic extrusion.

17. The apparatus of claim 16 wherein the delivery conduits are separated from one another by axial splits in said extrusion.

18. Apparatus for infusing an agent to a treatment site on the wall of a body lumen, said apparatus comprising:
   a flexible shaft having a proximal end and a distal end;
   an infusion array attached to the distal end of the flexible shaft and including a sleeve having an internal lumen and a plurality of delivery conduits disposed on or in said sleeve, wherein the sleeve is split between at least some adjacent pairs of delivery conduits.

19. Apparatus as in claim 18, wherein the sleeve is split fully between some adjacent pairs and partially between other adjacent pairs.

20. Apparatus as in claim 19 having at least one alternate adjacent pair of conduits, wherein the sleeve between alternate adjacent pairs is split fully in one pair and split in two sections in another pair.

21. Apparatus as in claim 20, wherein the sleeve has four attached delivery conduits with the sleeve split fully between a first opposed conduit pairs and into two sections between a second opposed conduit pairs.

22. Apparatus as in claim 21, wherein the splits in the second opposed conduit pairs remain connected near their middles.

23. Apparatus for infusing an agent to a treatment site on the wall of a body lumen, the apparatus comprising:
   a flexible shaft having a distal end and a proximal end, with a guide passage and a plurality of fluidly independent delivery passages extending axially through the shaft, the guide passage being open at the distal end;
   an inflation tube slidably disposed in the guide passage having a distal end, a proximal end, an axial inflation lumen therebetween, and an expansion member attached to the distal end in communication with the inflation lumen, wherein the expansion member may be advanced distally from the distal end of the shaft; and
   a plurality of laterally-deflectable delivery conduits attached to the distal end of the shaft generally parallel thereto, each delivery conduit having an axial lumen in communication with at least one of the delivery passages and a plurality of orifices on a lateral surface thereof, wherein the expansion member is axially positionable adjacent to the delivery conduits for laterally positioning the delivery conduits in apposition to the treatment site;
   and, wherein at least a first of the delivery conduits is in communication with a different delivery passage than at least a second of the delivery conduits so as to allow independent delivery of agents to the first and second delivery conduits; and means for maintaining relative alignment of the delivery conduits during lateral deflection thereof, wherein said means biases the delivery conduits to an undeflected configuration.

24. The apparatus of claim 23 wherein the alignment maintaining means comprises a tubular elastomeric sleeve, the delivery conduits being secured to the sleeve.

25. The apparatus of claim 24 wherein the elastomeric sleeve is disposed interior to the delivery conduits, the delivery conduits being secured to an exterior surface of the sleeve.

26. The apparatus of claim 24 wherein the elastomeric sleeve is disposed exterior to the delivery conduits, the delivery conduits being secured to an interior surface of the sleeve, wherein the orifices extend from the axial lumens of the delivery conduits through the sleeve.

27. The apparatus of claim 24 wherein the delivery conduits are arranged in adjacent pairs and wherein the tubular elastomeric sleeve is axially split between at least some of the adjacent pairs of the delivery conduits.

28. The apparatus of claim 27 wherein the tubular elastomeric sleeve is split fully between some adjacent pairs and partially between other adjacent pairs.

29. The apparatus of claim 28 wherein the tubular elastomeric sleeve is split fully to form two separate sections between alternate adjacent pairs.

30. The apparatus of claim 29 wherein the tubular elastomeric sleeve has four attached delivery conduits with the elastomeric tubular sleeve being split fully between first opposed conduit pairs and into two sections between second opposed conduit pairs.

31. The apparatus of claim 30 wherein the splits in the second opposed conduit pairs remain connected near their middles.

32. The apparatus of claim 23 wherein the alignment maintaining means comprises a stiffening element disposed axially in at least one delivery conduit.

33. The apparatus of claim 32 wherein the stiffening element comprises an axially rigid, laterally flexible rod.

34. The apparatus of claim 33 wherein the stiffening element has a geometry selected to provide low bending stiffness about a first axis perpendicular to the shaft, but high bending stiffness about a second axis perpendicular to the shaft and perpendicular to the first axis.

35. The apparatus of claim 33 wherein the rod is a resilient metal.

36. The apparatus of claim 32 wherein the stiffening element is embedded in the wall of the delivery conduit.

37. The apparatus of claim 32 wherein the stiffening element is disposed in the axial lumen of the delivery conduit.

38. The apparatus of claim 32 wherein the stiffening element is secured to the exterior of the delivery conduit.

39. The apparatus of claim 32 wherein at least a portion of stiffening element is radiopaque.

40. The apparatus of claim 23 further comprising means for maintaining patency of the axial lumen of each delivery conduit.

41. The apparatus of claim 40 wherein the means for maintaining patency comprises a flexible rod disposed axially in the axial lumen of at least one of the delivery conduits.

42. The apparatus of claim 41 wherein the rod is a resilient metal.

43. The apparatus of claim 23 further comprising a flexible distal tip having a proximal end secured to the distal end of the shaft, an open distal end, and an axial passage between the proximal and distal ends aligned with the guide passage of the catheter.

44. The apparatus of claim 43 wherein the distal tip is conically tapered such that the distal end has a smaller diameter than the proximal end.

45. The apparatus of claim 43 wherein the axial passage of the distal tip is conically tapered such that the axial passage has a diameter at the open distal end which is larger than the diameter of the guide passage.

46. The apparatus of claim 43 wherein the proximal end of the flexible distal tip comprises a plurality of prongs extending proximally from the tip and received in the axial lumens of the delivery conduits.

47. The apparatus of claim 46 further comprising at least one stiffening element disposed in the axial lumen of at least one delivery conduit, a distal end of the stiffening element being secured to one of said prongs of said distal tip.

* * * * *